(12) United States Patent  
Pellikka et al.

(10) Patent No.: US 8,137,540 B2  
(45) Date of Patent: Mar. 20, 2012

(54) METHODS AND APPARATUS FOR CONTINUOUS LARGE-SCALE RADIOLABELING

(75) Inventors: Raimo Pellikka, Moriken (CH); Steven W. King, Rancho Santa Margarita, CA (US); Peter Bläuenstein, Untersiggenthal (CH); Pius A. Schubiger, Lengnau (CH)

(73) Assignee: Peregrine Pharmaceuticals, Inc., Tustin, CA (US)

( * ) Notice: Subject to any disclaimer, the term of this patent is extended or adjusted under 35 U.S.C. 154(b) by 0 days.

(21) Appl. No.: 12/545,040

(22) Filed: Aug. 20, 2009

(65) Prior Publication Data

US 2009/0312523 A1 Dec. 17, 2009

Related U.S. Application Data

(62) Division of application No. 10/877,959, filed on Jun. 25, 2004, now Pat. No. 7,591,953.

(60) Provisional application No. 60/482,387, filed on Jun. 25, 2003, provisional application No. 60/493,121, filed on Aug. 7, 2003, provisional application No. 60/493,689, filed on Aug. 8, 2003.

(51) Int. Cl.  
*B01D 17/12* (2006.01)

(52) U.S. Cl. ..... 210/101; 29/896.6; 210/143; 210/198.2; 210/205; 210/258; 210/263; 210/321.6; 366/150.1; 417/475; 417/477.1; 422/159; 422/616; 424/1.21

(58) Field of Classification Search ............... 210/198.1, 210/198.2, 205, 258, 259, 263, 287, 321.6, 210/502.1, 143, 101, 206; 366/150.1, 160.2, 366/160.3; 417/477.1, 475; 422/110, 159, 422/501, 527, 534, 535, 608, 616–618; 600/3–5, 600/420; 424/1.11, 1.29, 1.33, 1.21, 1.37; 29/896.6, 896.62  
See application file for complete search history.

(56) References Cited

U.S. PATENT DOCUMENTS 3,816,033 A * 6/1974 Fried et al. .................... 417/429  
4,205,050 A * 5/1980 Piehl et al. .................... 423/228  
(Continued)

FOREIGN PATENT DOCUMENTS

CA 2 345 838 A1 7/2002  
(Continued)

OTHER PUBLICATIONS

Pellikka et al., "A New Continuous Large scale Method for Protein Labeling," *J. Labelled Compounds and Radiopharmaceuticals*, 46(Supp 1):S220, Aug. 10-14, 2003.

(Continued)

*Primary Examiner* — Joseph Drodge  
(74) *Attorney, Agent, or Firm* — Shelley P. M. Fussey

(57) ABSTRACT

Disclosed are improved methods and apparatus for radiolabeling, particularly methods and apparatus for large scale in-line radiolabeling of products, such as proteins and antibodies.

27 Claims, 11 Drawing Sheets

U.S. PATENT DOCUMENTS

| | | | | | |
|---|---|---|---|---|---|
| 4,301,139 | A | * | 11/1981 | Feingers et al. | 436/500 |
| 4,401,646 | A | * | 8/1983 | Rhodes et al. | 424/1.49 |
| 4,472,371 | A | * | 9/1984 | Burchiel et al. | 424/1.49 |
| 4,775,638 | A | | 10/1988 | Haisma | 436/547 |
| 4,874,601 | A | | 10/1989 | Flanagan | 422/101 |
| 4,945,042 | A | | 7/1990 | Geiger | 435/7.5 |
| 5,206,346 | A | | 4/1993 | Taylor | 530/391.3 |
| 5,275,789 | A | | 1/1994 | Taylor | 422/159 |
| 5,450,847 | A | * | 9/1995 | Kampfe et al. | 600/420 |
| 5,580,541 | A | * | 12/1996 | Wells et al. | 424/1.11 |
| 5,605,671 | A | | 2/1997 | Lyle | 424/1.41 |
| 5,639,627 | A | | 6/1997 | Tanaka | 435/7.95 |
| 6,241,967 | B1 | * | 6/2001 | Sachse et al. | 424/9.321 |
| 6,767,319 | B2 | * | 7/2004 | Reilly et al. | 600/5 |
| 7,591,953 | B2 | * | 9/2009 | Pellikka et al. | 210/758 |
| 2002/0102208 | A1 | | 8/2002 | Chinn et al. | 424/1.53 |
| 2003/0220470 | A1 | | 11/2003 | Govindan | 530/345 |

FOREIGN PATENT DOCUMENTS

| | | |
|---|---|---|
| EP | 1 160 241 | 12/2001 |
| WO | WO 82/03076 | 9/1982 |
| WO | WO 97/07126 | 2/1997 |
| WO | WO 02/04921 | 1/2002 |

OTHER PUBLICATIONS

Nemeth et al., "Preparation of Mono-$^{125}$I-labelled Gastrin-17 for Radioimmunoassay Measurements," *J. Labelled Compounds and Radiopharmaceuticals*, 43:855-863, 2000.

Visser et al., "Optimal Quality $^{131}$I-Monoclonal Antibodies on High-Dose Labeling in a Large Reaction Volume and Temporarily Coating the Antibody with IODO-GEN," *J. Nucl. Med.*, 42(3):509-519, 2001.

International Search Report for counterpart application PCT/US2004/020492, mailed Jan. 26, 2005.

Parseghian et al., Abstract # 652734 and Poster, "Proof of Principle Studies for an 'In-Line Radiolabelling' Method that Allows Large Scale Protein Labeling", Society of Nuclear Medicine 52$^{nd}$ Annual Meeting, Jun. 18-22, 2005, Toronto, Canada, Abstract (4 pages) and Poster (1 page).

Supplemental European Search Report for Application Serial No. EP 08010871, dated Aug. 18, 2008.

Harris et al., "In-Line Radiolabelling: A Novel Continuous-Flow System for Commercial-Scale Protein Labeling", *J. Nucl. Med.*, 50(7):1178-1186, 2009.

* cited by examiner

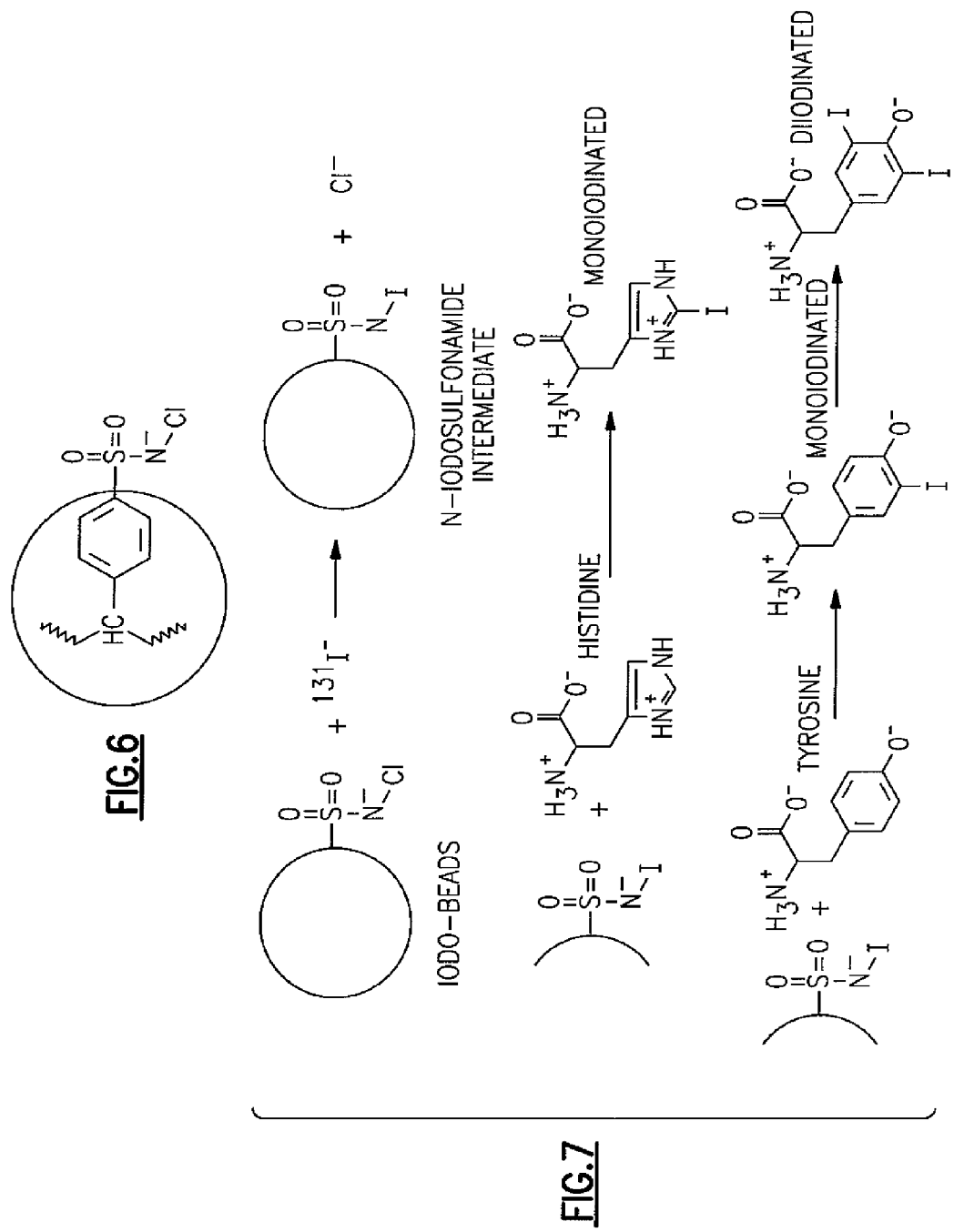

US 8,137,540 B2

METHODS AND APPARATUS FOR CONTINUOUS LARGE-SCALE RADIOLABELING

The present application is a divisional of U.S. application Ser. No. 10/877,959, filed Jun. 25, 2004, which issued as U.S. Pat. No. 7,591,953 on Sep. 22, 2009, which claims priority to first U.S. provisional application Ser. No. 60/482,387, filed Jun. 25, 2003, second U.S. provisional application Ser. No. 60/493,121, filed Aug. 7, 2003, and third U.S. provisional application Ser. No. 60/493,689, filed Aug. 8, 2003, the disclosures of each of which applications, including the specification, claims and drawings, are specifically incorporated herein by reference in their entireties without disclaimer.

BACKGROUND OF THE INVENTION

1. Field of the Invention

The present invention relates generally to the field chemical modification of molecules and, in particular, provides improved methods and apparatus for radiolabeling of various substances including, but not limited to, proteins and peptides for use in the pharmaceutical industry. More specifically, but without restriction to the particular embodiments hereinafter described, this invention relates to methods and apparatus for continuous large-scale radiolabeling of proteins and peptides.

2. Description of Related Art

Biotechnology plays an important role in medicine, agriculture and other areas of technology. Continued advances in such fields require ongoing biotechnological developments, such as increased and efficient production of radiolabeled materials, including for example proteins, such as antibodies and peptides, and other pharmaceuticals requiring modification involving electrophilic addition of desired molecules or elements such as a radiolabel.

Research aimed towards improving radiolabeling methods is ongoing. The prior art and currently available methods, however, all suffer from their particular deficiencies and drawbacks. These drawbacks include relatively low total activity, radiolysis of the product and the relatively low volume of the labeling batch.

Accordingly, to provide the type of radiolabeled materials required to promote ongoing biotechnological and biomedical developments, the art needs new and improved methods of radiolabeling materials, particularly proteins and antibodies. The development of large scale radiolabeling methods for use in the pharmaceutical industry is particularly sought after.

SUMMARY OF THE INVENTION

The present invention addresses long-felt needs in the art, and overcomes existing difficulties, by providing improved methods and apparatus for radiolabeling, particularly methods and apparatus for large scale radiolabeling for use in pharmaceutical, biomedical and other industries. The methods are able to radiolabel proteins, such as antibodies, with several GBq (gigabecquerel; 37 GBq=1 curie=$3.7 \times 10^{10}$ disintegrations per second) in a short production time.

The invention is therefore suitable for large scale, cost-effective production of radiopharmaceuticals for use as diagnostic and therapeutic agents. The methods and apparatus of the invention, and various exemplary and certain preferred embodiments thereof, are described in the present specification, claims and associated drawing figures and are exemplified in the working examples.

An exemplary apparatus or device of the invention is an apparatus or device, preferably a continuous mode radiolabeling apparatus or device, for labeling a biological component or molecule, such as a protein, polypeptide, peptide, antibody or antibody molecule, with at least a first radioactive label, preferably an oxidizable radioactive label. Such an apparatus or device may comprise:

at least a first reaction chamber or tube at least comprising a first end and a second end;

at least a first and second reagent vessel operatively, i.e., fluidly, connected or attached to the first end of the reaction chamber or tube; more particularly:

a first reagent vessel operatively, i.e., fluidly, connected or attached to the first end of the reaction chamber or tube through a first reagent or delivery tubing, the first reagent tubing connected to at least a first pump; and a second reagent vessel operatively, i.e., fluidly, connected or attached to the first end of the reaction chamber or tube through a second reagent or delivery tubing, the second reagent tubing connected to a pump; and at least a first purification unit at least comprising an inlet and an outlet, the inlet of the purification unit operatively, i.e., fluidly, connected or attached to the second end of the reaction chamber or tube.

The "first end and second end" of the at least a first reaction chamber or tube may be described as an "input terminus and an output terminus". The at least a "first and second reagent vessel", and any other reagent vessels, may be described as a "first and second reservoir" and any other "reservoirs". Examples of reagent vessels and reservoirs are "vials". Any such vials will be termed "reagent vials", as distinct from any "collection vials" used in conjunction with the apparatus or device.

Accordingly, the apparatus, or continuous mode radiolabeling apparatus or device, may comprise at least a first reaction chamber or tube comprising an input terminus and an output terminus; at least a first and second reservoir, each operatively attached to the input terminus of the reaction tube; and at least a first purification unit operatively attached to the output terminus of the reaction tube.

At least one of the reagent vessels or reservoirs may be comprised within a "radioshield", such as a lead shield. Typically, a reagent vessel or reservoir that comprises, or is intended or designed to comprise, at least one radioactive label, preferably an oxidizable radioactive label, or at least a composition, fluid or solution comprising at least one radioactive or oxidizable radioactive label, will be the reagent vessel or reservoir comprised within any radioshield or lead shield.

The "operative" connections or attachments may be described as "fluid", "fluidic" or "fluxive" connections or attachments, so that components that are "operatively connected or attached" are "fluidly or fluidically connected or attached", such that fluid can move, pass, passage or flow effectively between the connected or attached components.

It will be understood that the operative, fluid and fluidic connections and attachments are "controlled" operative, fluid and fluidic connections and attachments. That is, the operative, fluid and fluidic connections and attachments "permit" fluid to move, pass, passage or flow between the connected or attached components "under controlled conditions", i.e., conditions controlled directly or indirectly by the operator, including under conditions controlled by an operator, a computer or computer program. Thus, an operative, fluid or fluidic connection or attachment does not imply that a fluid will naturally move, pass, passage or flow between the connected or attached components under all conditions at all times, but only as directed, such as by an operator, computer or computer program.

In the operation of an apparatus or device of the invention, the operative, fluid or fluidic connections and attachments between the components will typically be operated or controlled such that the fluid moves, passes, passages or flows between the connected or attached components in a "directional" manner. That is, fluid will typically move, pass, passage or flow "from" one point "to" another point and/or move, pass, passage or flow "through" a component and/or "through" the apparatus or device as a whole. This notwithstanding, the operative, fluid or fluidic connections and attachments do not need to be "unidirectional" connections and attachments, as directional control can be imparted or achieved in the operation of the apparatus or device.

In the apparatus or device, and in their operation in the methods of the invention, the and solution(s) can move, pass, passage or flow and typically "react". Preferably, the reaction chamber or tube is a "reaction tube".

The reaction chamber or tube, preferably tube, may be of a predetermined or preselected length and a predetermined or preselected diameter. Such "predetermined or preselected lengths and diameters" are typically determined, selected or chosen so that, in the operation of the apparatus or device in the methods of the invention, the reaction tube is of a length and diameter effective to allow contact of the applied components effective to produce a desired amount of the radiolabeled molecule per unit time.

In the apparatus or device, and in their operation in the methods of the invention, the apparatus or device may comprise and be operated with a first and second reagent vessel or reservoir, with a first, second and third reagent vessel or reservoir, or with four, five or more reagent vessels or reservoirs. The currently preferred embodiments are wherein the apparatus or device comprises and/or is operated with a first and second reagent vessel or reservoir; and wherein the apparatus or device comprises and/or is operated with a first, second and third reagent vessel or reservoir. An apparatus or device that comprises a first, second and third reagent vessel or reservoir may still be operated in a mode that utilizes only the first and second reagent vessels or reservoirs thereof.

Whether the apparatus or device comprises a first and second reagent vessel or reservoir, or a first, second and third reagent vessel or reservoir or more, each of the reagent vessels or reservoirs may be operatively or fluidly connected or attached to the first end of the reaction chamber or tube using a single pump or using more than one pump. Preferably, the reagent vessels or reservoirs are operatively or fluidly connected or attached to the first end of the reaction chamber or tube using "reagent tubing or tubings" in conjunction with a single pump or two or more pumps.

Thus, in the apparatus or device, and in their operation in the methods of the invention, a first reagent vessel is operatively or fluidly connected or attached to the first end of the reaction chamber or tube through a first reagent tubing, the first reagent tubing connected to at least a first pump; and a second reagent vessel is operatively or fluidly connected or attached to the first end of the reaction chamber or tube through a second reagent tubing, the second reagent tubing connected to a pump, such as to the at least a first pump.

Each of the first and second reagent vessels or reservoirs may be operatively or fluidly connected or attached to the first end of the reaction chamber or tube, via their respective first and second reagent tubings, using the same, i.e., the first or at least a first pump. In such embodiments, the first or at least a first pump is preferably a multi-channel peristaltic pump.

Alternatively, each of the first and second reagent vessels or reservoirs may be operatively or fluidly connected or attached to the first end of the reaction chamber or tube, via their respective first and second reagent tubings, using distinct pumps, i.e., using at least a first and second pump. In such embodiments, the first and second pumps are preferably peristaltic pumps.

Optionally, a third reagent vessel is operatively or fluidly connected or attached to the first end of the reaction chamber or tube through a third reagent tubing, the third reagent tubing connected to a pump. In such an apparatus, the first, second and third reagent vessels may be operatively or fluidly connected or attached to the first end of the reaction chamber or tube via the same pump, typically a three channel peristaltic pump, operatively positioned between the reagent vessels and the first end of the reaction chamber or tube. Each of the first, second and third reagent vessels or reservoirs may variously be operatively or fluidly connected or attached to the first end of the reaction chamber or tube, via respective first, second and third reagent tubings, using distinct pumps, i.e., using at least a first, second and third pump. In such embodiments, the first, second and third pumps are preferably peristaltic pumps.

Irrespective of the number of pumps and their connections between the reagent vessels or reservoirs and the reaction chamber or tube, the pump or pumps are preferably controllable by a computer. In the apparatus or device, and in the operation of the apparatus or device in the methods of the invention, the use of one or more multi-channel peristaltic pumps that are controllable by a computer is thus preferred.

In addition to, or in place of, at least a first pump, the apparatus or device of the invention may comprise at least one other unit, device or means for moving fluid through the apparatus or device, typically in a controlled manner, and preferably for moving fluid through the apparatus or device to achieve substantially continuous flow. Such units, devices and means include those effective to move liquids by applying pressure and/or vacuum or other forces, such as rotational or centrifugal forces. At least one, two, three or more of such "controlled flow units" may thus be included, i.e., operatively positioned, in the apparatus or device of the invention.

In certain embodiments of the invention, including, but not limited to, where the apparatus or device comprises and/or is used in conjunction with two reagent vessels or reservoirs, the reaction chamber or tube may comprise or contain at least a first accessory labeling molecule or agent. An "accessory labeling molecule or agent", as used herein, is a substance, component, molecule or agent that assists, improves or facilitates the labeling process. Examples include chelators, and a preferred example is at least a first oxidation or "oxidizing agent", which is preferably used in conjunction with an oxidizable radioactive label.

Such reaction chambers or tubes will typically "comprise or contain" at least a first accessory labeling molecule or agent, preferably at least a first oxidizing agent, in a manner "effective to contact" fluid(s) or solution(s) that move, pass, passage or flow into, along or through the reaction chamber or tube. Typically, the "effective contact" does not significantly impede or retard the passage, progression or flow of fluid(s) or solution(s) into, along, through or out of the reaction chamber or tube. The contact is also "effective" for the accessory labeling molecule, agent or oxidizing agent to "react" with components in the fluid(s) or solution(s), and preferably, for the accessory labeling molecule, agent or oxidizing agent to react with components in the fluid(s) or solution(s) as they move, pass, passage or flow into, along or through the reaction chamber or tube.

One such embodiment of reaction chamber or tube is a reaction chamber or tube in which at least a portion, preferably a substantial or significant portion, of the inner surface of the chamber or tube is coated with at least a first accessory labeling molecule or agent, preferably at least a first oxidizing agent. Thus, the invention provides an apparatus or device, and methods of using the apparatus or device, wherein at least a first reaction chamber or tube comprises a first end, a second end, an outer surface and an inner surface; and wherein at least a portion, substantial or significant portion of the inner surface is coated with at least a first accessory labeling molecule or agent, preferably an oxidizing agent.

"Coated with", in this context, thus means an inner surface in which at least a portion, and preferably a substantial or significant portion, is "operatively attached" to at least a first accessory labeling molecule or agent, preferably an oxidizing agent. An example of an oxidizing agent that may be coated onto, or operatively attached to, such a chamber or tube inner surface is 1,3,4,6-Tetrachloro-3α,6α-diphenylglycouril.

Another embodiment of such a reaction chamber or tube is a reaction chamber or tube that comprises or contains an immobilized accessory labeling molecule or agent, preferably at least a first oxidizing agent, not attached to the inner surface of the chamber or tube. Such "immobilized" accessory labeling molecules, agents or oxidizing agents include accessory labeling molecules, agents or oxidizing agents attached, i.e., "operatively attached" to an immobilizing substrate or substrates. The "immobilizing substrate or substrates" include any solid support material that can be operatively attached to the chosen accessory labeling molecule, agent or oxidizing agent and inserted into the reaction chamber or tube without significantly impeding or retarding the passage, progression or flow of fluid(s) or solution(s) into, along, through or out of the reaction chamber or tube.

Examples of such immobilizing substrates are meshes, fibers or fibrous solid supports and microparticles or beads, and populations thereof, wherein the structural component of the mesh(es), fiber(s), microparticle(s) or bead(s) is operatively attached to the at least a first accessory labeling molecule or agent, preferably to the at least a first oxidizing agent. A fibrous immobilizing substrate or solid support may comprise natural fibers, including cotton, or synthetic fibers and/or polymers, or mixtures thereof. An example of an oxidizing agent that may be operatively attached to a mesh(es), fiber(s), microparticle(s) or bead(s) in this manner is N-chlorotoluenesulfonamide.

An exemplary apparatus or device of the invention is thus an apparatus or device comprising:
  a reaction chamber or tube comprising a first end and a second end;
  a first reagent vessel fluidly connected to the first end of the reaction chamber or tube through a first reagent tubing, the first reagent tubing connected to at least a first pump;
  a second reagent vessel fluidly connected to the first end of the reaction chamber or tube through a second reagent tubing, the second reagent tubing connected to a pump; and
  at least a first purification unit comprising an inlet and an outlet, the inlet of the purification unit fluidly connected to the second end of the reaction chamber or tube.

Another exemplary apparatus or device of the invention is an apparatus or device comprising:
  a reaction chamber having a first end and a second end;
  a first reagent vessel fluidly connected to the first end of the reaction chamber through a first reagent tubing, the first reagent tubing connected to a pump;
  a second reagent vessel fluidly connected to the first end of the reaction chamber through a second reagent tubing, the second reagent tubing connected to the pump;
  a third reagent vessel fluidly connected to the first end of the reaction chamber through a third reagent tubing, the reagent tubing connected to the pump;
  a purification column having an inlet and an outlet, the inlet of the purification column fluidly connected to the second end of the reaction chamber; and
  a collection vessel connected to the outlet of the purification column.

A further exemplary apparatus or device of the invention is an apparatus or device comprising:
  a reaction chamber or tube comprising a first end and a second end;
  a first reagent vessel fluidly connected to the first end of the reaction chamber or tube through a first reagent tubing, the first reagent tubing connected to a pump;
  a second reagent vessel fluidly connected to the first end of the reaction chamber or tube through a second reagent tubing, the second reagent tubing connected to the same pump;
  a third reagent vessel fluidly connected to the first end of the reaction chamber or tube through a third reagent tubing, the reagent tubing connected to the same pump; and
  at least a first purification unit comprising an inlet and an outlet, the inlet of the purification unit fluidly connected to the second end of the reaction chamber or tube.

Yet a further exemplary apparatus or device of the invention is an apparatus or device comprising:
  a reaction chamber or tube comprising a first end and a second end;
  a first reagent vessel fluidly connected to the first end of the reaction chamber or tube through a first reagent tubing, the first reagent tubing connected to a first pump;
  a second reagent vessel fluidly connected to the first end of the reaction chamber or tube through a second reagent tubing, the second reagent tubing connected to a second pump;
  a third reagent vessel fluidly connected to the first end of the reaction chamber or tube through a third reagent tubing, the reagent tubing connected to a third pump;
  at least a first purification unit comprising an inlet and an outlet, the inlet of the purification unit fluidly connected to the second end of the reaction chamber or tube.

The first, second and third pumps in the foregoing apparatus or device are preferably peristaltic pumps. The first, second and third pumps in the foregoing apparatus or device are also preferably each controllable by a computer.

Still a further exemplary apparatus or device of the invention is an apparatus or device comprising:
  a reaction chamber or tube comprising a first end, a second end, an outer surface and an inner surface;
  a first reagent vessel fluidly connected to the first end of the reaction chamber or tube through a first reagent tubing, the first reagent tubing passing through at least a first pump;
  a second reagent vessel fluidly connected to the first end of the reaction chamber or tube through a second reagent tubing, the second reagent tubing passing through a pump; and
  at least a first purification unit comprising an inlet and an outlet, the inlet of the purification unit fluidly connected to the second end of the reaction chamber or tube.

Regarding the foregoing apparatus or device, at least a first oxidizing agent is may be bound to at least a portion of the inner surface of the reaction chamber or tube. The oxidizing agent may be 1,3,4,6-Tetrachloro-3α,6α-diphenylglycouril. Such an apparatus or device may also further comprise microparticles attached to at least a first oxidizing agent, wherein the microparticles are comprised within the reaction chamber or tube. Exemplary microparticles are those attached to the oxidizing agent, N-chlorotoluenesulfonamide.

In the apparatus or device of the invention, and in their operation in the methods of the invention, the "purification unit" may be any one or more purification components or devices capable of substantially purifying a radiolabeled component or molecule. That is, at least a first purification component or device capable of, or effective in, substantially separating a radiolabeled component or molecule from any free radiolabel; any remaining components of the radiolabeling process or reaction, such as accessory labeling molecules or agents, e.g., oxidizing agents; and any other unlabeled components or molecules.

For example, one or more purification components or devices capable of substantially separating a radiolabeled protein, polypeptide, peptide, antibody or antibody molecule from any free oxidizable radioactive label, any remaining oxidizing agent and any unlabeled protein, polypeptide, peptide, antibody or antibody molecule. In certain embodiments of the apparatus, device and methods of the invention, the purification unit comprises at least a first substance that binds iodine, mixed halogen species, and oxidized iodide species.

The purification unit or units of the present apparatus, device and methods may comprise at least a first component or device in which the purification mechanism includes separation on the basis of charge, such as at least a first ion exchange column or anion exchange column. The purification unit or units may also comprise at least a first component or device in which the purification mechanism includes separation on the basis of size, such as at least a first size exclusion or gel filtration column. Affinity columns and other purification tools or equipment may also be used. Furthermore, the purification unit or units may comprise at least a first dialysis unit. Such a dialysis unit will typically comprise an inlet and an outlet, with the inlet of the dialysis unit fluidly connected to the second end of the reaction chamber or tube.

Although not necessary for the successful operation of the invention, the apparatus, devices and methods may utilize a purification unit that comprises two or more purification devices or units, such as at least a first and second, or at least a first, second and third, purification device or column connected in sequence. For example, a component that separates mainly on the basis of charge may be used in combination with a component that separates mainly on the basis of size, or a component that separates mainly based on charge may be used in combination with a dialysis unit.

In the apparatus or device of the invention, and in their operation in the methods of the invention, the apparatus or device may also comprise at least a first dispensing unit or collection vessel. Any dispensing unit or collection vessel is directly or indirectly connected, i.e., operatively and fluidly connected, to the outlet of the purification unit. Where a dialysis unit is present, the inlet of the dialysis unit is typically fluidly connected to the second end of the reaction chamber or tube and the outlet of the dialysis unit may then be connected to the collection vessel.

At least a first filter, preferably a sterile filter, may also be used in the apparatus, devices and methods of the invention. Preferably, such a filter is also operatively or fluidly connected to the outlet of the purification unit. In certain preferred embodiments, the filter disposed between the at least a first purification unit and any dispensing unit or collection vessel. For example, the invention provides apparatus, devices and methods that utilize a filter comprising an input end and an output end; the input end of the filter fluidly connected to the outlet of the purification unit; and the output end of the filter connected to a collection vessel.

The apparatus or device of the invention, and particularly the methods of the invention, may be used to radiolabel essentially any substance or molecule. That is, any substance or molecule that can undergo a radiolabeling reaction. As used herein, a "target" substance, component or molecule means the "substance, component or molecule to be radiolabeled". Preferred examples of target substances for radiolabeling according to the invention are biological components and molecules, such as, but not limited to proteins, polypeptides, peptides, antibodies and antibody molecules.

The terms "antibody", "antibody molecules" and "immunoglobulin", as used herein, refer generally to any antibody-based binding agent, including polyclonal and monoclonal antibodies. Included are antibodies of the five major classes, IgA, IgD, IgE, IgG, and IgM, further including antibodies of any subclass or isotype, such as IgG1, IgG2, IgG3, IgG4 and the like. Thus, antibodies are included in which the heavy-chain constant domains are α, δ, ε, γ and μ; and in which the light chains are kappa (κ) or lambda (λ).

Devices, apparatus and methods of the invention may particularly be used to radiolabel monoclonal antibodies (MAbs) and derivatives thereof, including monoclonal antibodies of the murine, human, monkey, rat, hamster, rabbit, frog and chicken origin. Radiolabeling murine, human or humanized monoclonal antibodies will often be preferred. Radiolabeling humanized, part-human or human antibodies is particularly encompassed.

Radiolabeling an "antibody" or "antibody molecules", as used herein, covers radiolabeling all antibodies from all species, and antigen binding fragments thereof, including dimeric, trimeric and multimeric antibodies; bispecific antibodies; chimeric antibodies; human and humanized antibodies; recombinant, engineered and camelized (camelised) antibodies, and fragments thereof. Particularly included is radiolabeling antibody fragments such as Fab', Fab, F(ab')$_2$, single domain antibodies (DABs), complementarity determining regions (CDRs), CDR1-3, Fv, scFv (single chain Fv), linear antibodies, diabodies, camelized antibodies and the like.

By way of example only, the apparatus or device of the invention, and particularly the methods of the invention, may be used to radiolabel a targeting agent or component, such as a protein, polypeptide, peptide, antibody or antibody molecule, which binds to a component expressed, accessible to binding or localized on the surface of a tumor cell or to a component released from a necrotic tumor cell. As further examples, the apparatus or device of the invention, and particularly the methods of the invention, may be used to radiolabel a targeting agent or component, such as a protein, polypeptide, peptide, antibody or antibody molecule, which binds to a component expressed, accessible to binding or localized on the surface of tumor vasculature, intratumoral vasculature or tumor stroma. Such targeting agents are disclosed, by way of example only, in U.S. Pat. Nos. 6,093,399, 6,004,555, 5,877,289, 6,036,955 and 6,749,853; and 5,019, 368, 4,861,581 and 5,882,626; and 6,004,554, 5,965,132, 5,855,866, 5,776,427, 5,863,538, 6,051,230, 6,261,535 and 5,660,827; and 6,406,693; and 6,312,694; and 6,342,219, 6,342,221, 6,416,758, 6,524,583, 6,676,941 and 6,703,020; each specifically incorporated herein by reference.

In addition to proteins, polypeptides, peptides, and antibody molecules, other molecules that can undergo electrophilic substitution reactions may be labeled in the invention. Biological components and molecules that include, or can be modified to comprise, at least a first group that can undergo electrophilic substitution reactions are particularly included. Thus, lipids, carbohydrates, glycoproteins, proteoglycans and a wide range of small molecules can be radiolabeled using the present invention.

Although particularly suitable for use with iodine labels, e.g., in radioiodination, the apparatus, devices and methods of the invention may be used to label a substance, component or molecule with a range of other labels, particularly when used in conjunction with any required accessory labeling agents. Thus, technetium$^{99m}$, indium$^{111}$, rhenium$^{188}$, rhenium$^{186}$, copper$^{64}$, copper$^{67}$, yttrium$^{90}$, astatine$^{211}$ and gallium$^{67}$, for example, can be used in the invention.

Isotopes capable of being oxidized to form the mixed halogen species are preferred for use in the present invention. In terms of iodine, the apparatus, devices and methods of the invention may be used in conjunction with iodine$^{123}$, iodine$^{124}$, iodine$^{125}$ or iodine$^{131}$; preferably, wherein the radioactive label is iodine-131 or iodine-125; and most preferably, wherein the radioactive label is iodine-131.

Turning to the methods of the invention in particular, the invention provides methods for preparing at least a first radiolabeled substance, component or molecule, such as a biological substance, component or molecule, e.g., one or more proteins, polypeptides, peptides, antibodies and antibody molecules. The methods generally comprise passing effective amounts of the substance, component or molecule to be radiolabeled and the radioactive label, along with effective amounts of any accessory labeling molecules or agents required or preferred for the reaction, through an apparatus or device in accordance with the invention. The "passing through the apparatus or device" is carried out under conditions and for a period of time effective to produce a radiolabeled substance, component or molecule. The resultant radiolabeled substance, component or molecule so produced is then collected from the apparatus or device.

In a currently preferred embodiment, the methods comprise passing effective amounts of the substance, component or molecule to be radiolabeled and an oxidizable radioactive label through an apparatus or device in accordance with the invention in the presence of an effective amount of an oxidizing agent. The "passing through the apparatus or device in the presence of an effective amount of an oxidizing agent" is carried out under conditions and for a period of time effective to oxidize the oxidizable radioactive label and in a manner suitable to produce a radiolabeled substance, component or molecule. The resultant radiolabeled substance, component or molecule so produced is then collected from the apparatus or device.

Accordingly, the methods for preparing at least a first radiolabeled substance, component or molecule, may comprise:

passing an effective amount of at least a first substance, component or molecule to be radiolabeled, or at least a first composition, fluid or solution comprising an effective amount of the substance, component or molecule to be radiolabeled, and an effective amount of at least one oxidizable radioactive label, or at least a second composition, fluid or solution comprising an effective amount of the oxidizable radioactive label, through at least a first reaction chamber or tube in the presence of an effective amount of at least a first oxidizing agent;

allowing the at least a first oxidizing agent, at least one oxidizable radioactive label and at least a first substance, component or molecule to react during passage through the reaction chamber or tube, thereby producing a radiolabeled molecule; and collecting the radiolabeled molecule after passage through the reaction chamber.

Such methods may be described as those comprising:

passing an effective amount of a substance, component or molecule to be radiolabeled, and an effective amount of an oxidizable radioactive label through a reaction chamber or tube in the presence of an effective amount of an oxidizing agent;

allowing the oxidizing agent, oxidizable radioactive label and substance, component or molecule to react during passage through the reaction chamber or tube, thereby producing a radiolabeled molecule; and collecting the radiolabeled molecule after passage through the reaction chamber.

"Passing through" the reaction chamber or tube and "allowing" the oxidizing agent, oxidizable radioactive label and substance, component or molecule to "react during passage through" the reaction chamber or tube means that the progression of the components through the reaction chamber or tube, or the apparatus or device as a whole, is carried out under conditions and for a period of time effective to produce a radiolabeled substance, component or molecule. The passing or applying "into and out of" or "passing through" the reaction chamber or tube, or the apparatus as a whole, is thus an active process, rather than the static "batch mode" processes of the prior art and current apparatus, devices and methods.

The radiolabeling methods preferably comprise "applying" or "passing" effective amounts of the substance, component or molecule to be radiolabeled and the oxidizable radioactive label into or through the reaction chamber or tube, in the presence of an effective amount of an oxidizing agent, in a manner "effective to substantially continuously mix" the components. That is, in a manner suitable and for a period of time effective to substantially continuously mix the substance, component or molecule to be radiolabeled, the oxidizable radioactive label and the oxidizing agent, i.e., to "substantially maintain effective contact" between these components, during passage along or through the reaction chamber or tube. The "effective contact" between these components is "effective, reactive contact" or "reactive contact", i.e., contact effective to permit or facilitate the radiolabeling reaction, thereby radiolabeling the substance, component or molecule.

Radiolabeling methods of the invention may thus comprise:

flowing an effective amount of the substance, component or molecule to be radiolabeled, or at least a first composition, fluid or solution comprising the substance, component or molecule to be radiolabeled, and an effective amount of at least one oxidizable radioactive label, or at least a second composition, fluid or solution comprising an effective amount of the oxidizable radioactive label, through a reaction chamber or tube in the presence of an effective amount of an oxidizing agent, thereby preparing a radiolabeled molecule; and obtaining the radiolabeled molecule from the outflow of the reaction chamber or tube.

Similarly, the radiolabeling methods of the invention may comprise:

substantially continuously inflowing an effective amount of the substance, component or molecule to be radiolabeled, or at least a first composition, fluid or solution comprising an effective amount of the substance, component or molecule to be radiolabeled, and an effective amount of at least one oxidizable radioactive label, or at least a second composition, fluid or solution comprising an effective amount of the oxidizable radioactive label, into a reaction chamber or tube in the presence of an effective amount of an oxidizing agent;

allowing the oxidizing agent, the oxidizable radioactive label and the substance, component or molecule to react within the reaction chamber or tube, thereby producing a radiolabeled molecule; and substantially continuously outflowing the radiolabeled molecule from the reaction chamber or tube, thereby obtaining the radiolabeled molecule.

Concerning the reaction chamber or tube, the use of a reaction tube is generally preferred. The reaction tube is preferably of a predetermined or preselected length and a predetermined or preselected diameter. Such predetermined or preselected lengths and diameters are typically determined, selected or chosen so that the reaction tube is of a length and diameter suitable to allow contact of effective amounts of the substance, component or molecule to be radiolabeled, the oxidizable radioactive label and the oxidizing agent in a manner effective to produce a desired amount of the radiolabeled molecule per unit time.

Any effective method for applying, passing into and out of, passing through, substantially continuously mixing, substantially maintaining effective or reactive contact, flowing into, out of and through, and inflowing and outflowing may be employed in the invention, so long as at least a first composition, fluid or solution substantially continuously passes or flows through or along the reaction chamber or tube, or the apparatus or device as a whole during operation of the method. A currently preferred method of achieving substantially continuous flow is to use at least a first pump.

Alternatively, pressure and/or vacuum or other forces such as rotational or centrifugal forces may be used to move fluid through the radiolabeling apparatus of the present invention. Thus, one or more of the reactants may be pneumatically moved through the reaction chamber or tube, and the apparatus or device as whole, using pressure (applied to the reagent vessels) or vacuum applied at the second end or outlet of the reaction chamber or tube. All such methods and modes of operation are encompassed in the methods of the invention, and in the corresponding apparatus and devices.

Accordingly, certain preferred radiolabeling methods of the invention are those wherein effective amounts of at least the substance, component or molecule to be radiolabeled and the oxidizable radioactive label are pumped through the reaction chamber or tube, and preferably, are substantially continuously pumped through the reaction chamber or tube. More preferably, effective amounts of at least the substance, component or molecule to be radiolabeled and the oxidizable radioactive label are pumped through, preferably substantially continuously pumped through, a reaction tube.

In the operation of the methods, as well as using a reaction tube of a predetermined or preselected length and diameter, effective amounts of the at least a first target substance, component or molecule and at least a first oxidizable radioactive label are each preferably pumped into the reaction chamber or tube at a predetermined or preselected flow rate. These methods may be described as those wherein at least a first composition, fluid or solution comprising an effective amount of the substance, component or molecule to be radiolabeled, and at least a second composition, fluid or solution comprising an effective amount of the oxidizable radioactive label are each pumped into the reaction chamber or tube at a predetermined or preselected flow rate.

The "predetermined or preselected flow rate" is typically a flow rate determined, selected or controlled to allow the oxidizing agent to oxidize the oxidizable radioactive label to form a reactive intermediate that reacts with a substituent of the target substance, component or molecule that can undergo electrophilic substitution, thereby producing a desired amount of the radiolabeled substance, component or molecule per unit time. Thus, the predetermined flow rate is controlled to allow the oxidizing agent to oxidize the oxidizable radioactive label to form a reactive intermediate that reacts with a substituent of the target substance, component or molecule that can undergo electrophilic substitution, thereby producing an admixture comprising the radiolabeled molecule. Preferably, the predetermined flow rate is selected to produce an admixture comprising a desired amount of the radiolabeled molecule without substantially damaging the radiolabeled molecule, e.g., by radiolysis.

In certain embodiments, the predetermined flow rate is a rate that provides sufficient or ample time for the oxidizing agent to oxidize the oxidizable radioactive label to form a mixed halogen species capable of reacting with tyrosine and histidine residues of a target proteinaceous substance, component or molecule to produce a radiolabeled proteinaceous substance, component or molecule. Here, the predetermined flow rate is preferably selected to form a mixed halogen species capable of reacting with tyrosine and histidine residues of a target protein to produce a radiolabeled protein without substantially damaging the radiolabeled molecule, e.g., without causing substantial radiolysis.

The predetermined flow rate may be controlled by controlling the one or more pumps. Thus "pumping" preferably means activating the one or more pumps at a predetermined rate to move the oxidizing agent, the target substance, component or molecule and the oxidizable radioactive label into, and preferably through, the reaction chamber or tube.

The one or more pumps operating in the methods are preferably one or more peristaltic pumps. Irrespective of the number of pumps, at least a first, second, third or more, and preferably each, pump is controllable or controlled by a computer. The methods preferably use at least a first multi-channel peristaltic pump controlled by a computer.

The number of pumps for use in the methods, apparatus and devices of the invention may vary according to the chosen embodiment. Such as, for example, in radiolabeling methods using an oxidizable radioactive label, the location of at least a first oxidizing agent may influence the choice of the number of reagent vessels or reservoirs and the choice of the number of pumps.

In methods using a first and second reagent vessel or reservoir, the first and second reagent vessel or reservoir may be operatively or fluidly connected to separate pumps, i.e., to a first and second pump, respectively. Alternatively, a first and second reagent vessel or reservoir may be operatively or fluidly connected to the same pump, i.e., to the at least a first, or the first pump. The same applies to methods using a first, second and third reagent vessel or reservoir. So that the first, second and third reagent vessel or reservoir may be operatively or fluidly connected to separate pumps, i.e., to a first, second and third pump, respectively. On the other hand, the first, second and third reagent vessel or reservoir may be operatively or fluidly connected to the same pump, i.e., to the at least a first, or the first pump. Typically, a pump operatively or fluidly connected or attached to two or more reagent vessels or reservoirs will be a multi-channel pump, preferably a multi-channel peristaltic pump.

Preferably, effective amounts of at least the substance, component or molecule to be radiolabeled and the radiolabel, preferably an oxidizable radioactive label, are pumped through the reaction chamber or tube, and more preferably, are maintained in separate reagent vessels or reservoirs and are pumped through the reaction chamber or tube by drawing from the separate reagent vessels or reservoirs. The substance to be radiolabeled and the radiolabel may be drawn or pumped from their separate reagent vessels or reservoirs using a single pump or two separate pumps.

There are generally more options for applying accessory labeling molecules or agents, particularly oxidizing agents, to the reaction chamber or tube. Such molecules or agents, preferably oxidizing agents, may be disposed in at least a one reagent vessel or reservoir and effective amounts thereof pumped into the reaction chamber or tube during execution of the method. An example of an oxidizing agent with suitable solubility for such use is N-chlorotoluenesulfonamide.

Thus, effective amounts of each of the substance, component or molecule to be radiolabeled, the oxidizable radioactive label and the oxidizing agent can be pumped through the reaction chamber or tube. Effective amounts of each of these three basic components may be pumped into the reaction chamber or tube from three separate reagent vessels or reservoirs. If desired, an effective amount of a mixture or admixture of the molecule to be radiolabeled and the oxidizing agent may be disposed within a first reagent vessel or reservoir and pumped into the reaction chamber or tube therefrom as a pre-mixture. In which case, the oxidizable radioactive label could be disposed within a second reagent vessel or reservoir and an effective amount pumped into the reaction chamber or tube therefrom in a coordinated manner.

Otherwise, an effective amount of an accessory labeling molecule or agent, preferably at least a first oxidizing agent, may be disposed, located or comprised within the reaction chamber or tube prior to executing the methods. Where at least a first oxidizing agent is already located within the reaction chamber or tube, the substance, component or molecule to be radiolabeled and the oxidizable radioactive label contact and react with the oxidizing agent upon entry into, and during passage along, the reaction chamber or tube.

Options for locating at least a first oxidizing agent within the reaction chamber or tube include wherein an effective amount of the oxidizing agent is present on at least a portion of the inner surface of the reaction chamber or tube, and preferably, on a substantial or significant portion of such inner surface. An exemplary oxidizing agent for use in such "coatings" is 1,3,4,6-Tetrachloro-3α,6α-diphenylglycouril.

Another option to locate at least a first oxidizing agent within the reaction chamber or tube is wherein an effective amount of the oxidizing agent is present on an immobilizing substrate, such as a mesh, fiber, fibrous solid support, or a population of microparticles contained within the reaction chamber or tube. An exemplary oxidizing agent for use in such "packings" is N-chlorotoluenesulfonamide.

As with the apparatus and devices of the invention, the methods of the invention are typically used with at least a first purification unit capable of substantially purifying a radiolabeled substance, component or molecule. The radiolabeled molecule exiting from the reaction chamber or tube is thus applied to at least a first purification unit and a substantially purified radiolabeled molecule is isolated therefrom.

Exemplary purification units include one or more ion exchange columns, anion exchange columns, gel filtration columns, affinity columns, dialysis units and combinations thereof. The composition, fluid or solution pumped from or out of the reaction chamber or tube, which comprises the radiolabeled product, is applied to the at least a first purification unit, thereby substantially separating the radiolabeled product from any other components therein. In particular, thereby separating the radiolabeled product from any remaining components of the radiolabeling reaction, such as oxidizing agents, oxidizable radioactive labels, reactive intermediates, and from any unlabeled starting materials. In application into a dialysis unit, the methods dialyze out any remaining components of the radiolabeling reaction, thereby producing substantially purified radiolabeled product.

One exemplary method within the invention is a method for use with an apparatus or device that comprises at least a first and second reagent vessel wherein such a method comprises:

placing a first solution or mixture comprising both a target molecule and an oxidizing agent into the first reagent vessel;

placing a second solution comprising an oxidizable radioactive label into the second reagent vessel;

pumping effective amounts of the first solution and the second solution through the reaction chamber or tube, wherein the target molecule, the oxidizing agent and the oxidizable radioactive label react during passage through the reaction chamber or tube, thereby producing an admixture comprising an effective amount of a radiolabeled molecule;

pumping the admixture through the purification unit; and collecting a substantially purified radiolabeled molecule from the purification unit.

In the foregoing method, "pumping" is preferably conducted at a predetermined flow rate using the pump. The predetermined flow rate is controlled throughout the method, to allow the oxidizing agent to oxidize the oxidizable radioactive label to form a reactive intermediate. The "reactive intermediate" is one capable of binding to a substituent of the target molecule that can undergo electrophilic substitution. "Binding to the substituent that can undergo electrophilic substitution" occurs under conditions and for a period of time effective to allow the reactive intermediate to "react with" the substituent to label the target molecule, thereby producing an effective amount of a radiolabeled molecule or product.

The radiolabeled "product" is preferably purified by pumping the mixture or solution containing the radiolabeled product from the reaction chamber or tube into the purification unit, such a purification column, to produce a substantially purified radiolabeled product. More preferably, the substantially purified radiolabeled product is filtered by pumping the substantially purified radiolabeled product through a filter, preferably a sterile filter, and the substantially purified, filtered radiolabeled product is collected.

Yet a further exemplary method within the invention is a method for use with an apparatus or device that comprises at least a first and second reagent vessels and an effective amount of at least a first oxidizing agent comprised within the reaction chamber or tube. Such a method comprises:

placing a first solution comprising a target molecule into the first reagent vessel;

placing a second solution comprising an oxidizable radioactive label into the second reagent vessel;

pumping the first solution and the second solution through the reaction chamber or tube, wherein the target molecule and the oxidizable radioactive label react with the oxidizing agent in the reaction chamber or tube during passage through the reaction chamber or tube, thereby producing an admixture comprising a radiolabeled molecule;

pumping the admixture through the purification unit; and collecting a substantially purified radiolabeled molecule from the purification unit.

Still a further exemplary method within the invention is a method for use with an apparatus or device that comprises at least a first, second and third reagent vessel, wherein such a method comprises:

placing an oxidizing agent into the first reagent vessel;
placing a target molecule into the second reagent vessel;
placing an oxidizable radioactive label into the third reagent vessel;
pumping effective amounts of the oxidizing agent, the target molecule and the oxidizable radioactive label through the reaction chamber or tube at a predetermined rate effective for the oxidizing agent to oxidize the oxidizable radioactive label to form a reactive intermediate that reacts with a substituent of the target molecule that can undergo electrophilic substitution, thereby producing an effective amount of a radiolabeled molecule;
purifying the radiolabeled molecule by passing the radiolabeled molecule through the purification unit; and
collecting a substantially purified radiolabeled molecule therefrom.

If chosen, the substantially purified radiolabeled molecule obtained from the purification unit(s) may be filtered through a filter, preferably a sterile filter, attached to the purification unit and a filtered, substantially purified radiolabeled molecule obtained thereafter. Such a filter may be disposed between the purification unit and any dispensing unit or collection vessel. When used in conjunction with at least a first dispensing unit or collection means and vessel(s), such a dispensing unit is directly or indirectly connected to the purification unit, such that operation of the method dispenses substantially purified or substantially purified and filtered radiolabeled substances, components or molecules into a chosen collection vessel or series of vessels or receptacles.

The methods of the invention may further comprise adding an effective amount of at least a first radioprotectant to the substantially purified or substantially purified and filtered radiolabeled substances, components or molecules. A "radioprotectant" is a component, molecule or agent capable of absorbing radiation. Preferably, a radioprotectant effectively absorbs radiation without significantly adversely affecting other components in contact with the radioprotectant, particularly the radiolabeled substance, component or molecule. Exemplary radioprotectants are serum albumins, such as bovine serum albumin and human serum albumin, and also ascorbate.

In the operation of such methods, an effective amount of the at least a first radioprotectant may be disposed within a chosen collection vessel or receptacle, and the substantially purified or substantially purified and filtered radiolabeled substance may be added to the radioprotectant simply by placing the radiolabeled substance into the chosen collection vessel or receptacle.

A series or plurality of vessels or receptacles, such as a series or plurality of vials, may be used, and the method operated such that an aliquot of the substantially purified or substantially purified and filtered radiolabeled substance is dispersed into each of the vessels, receptacles or vials. Any such one or series of vessels, receptacles or vials may be pre-loaded with an effective amount of one or more desired components, such as radioprotectants, pharmaceutical diluents or vehicles or such like.

Thus, the substantially purified or substantially purified and filtered radiolabeled substance may be dispersed into or collected in a pharmaceutically acceptable formulation, optionally one that also contains a radioprotectant, or into a plurality of such formulations. The methods may thus be used to prepare substantially purified or substantially purified and filtered radiolabeled substances, such as radiopharmaceuticals, dispersed into a plurality of collection vials, preferably so that each vial contains a pharmaceutically acceptable unit dose.

As described above, the methods of the invention may be used to radiolabel essentially any substance or molecule, such as any biological component or molecule, e.g., proteins, polypeptides, peptides, antibodies and antibody molecules, lipids, carbohydrates, glycoproteins, proteoglycans and small molecules. Methods of labeling molecules that can undergo electrophilic substitution reactions with one or more isotopes capable of being oxidized to form the mixed halogen species are preferred aspects of the invention. In methods to radiolabel proteins, polypeptides or peptides, such as antibodies and antibody molecules, the radioactive label may be operatively attached to one or more tyrosine, histidine or tryptophan residues in the protein, polypeptide or peptide.

In certain preferred embodiments, the invention provides methods to radiolabel a target molecule, preferably a protein, polypeptide, peptide, antibody or antibody molecule, with an iodine isotope. Such methods may comprise applying effective amounts of the target molecule and the iodine isotope to a reaction chamber or tube in the presence of an oxidizing agent in a manner effective to substantially continuously mix the target molecule, the iodine isotope and the oxidizing agent during passage along the reaction tube, thereby radiolabeling the target molecule with the iodine isotope.

A particular method for radioiodinating a protein, polypeptide, antibody or antibody molecule with an iodine radiolabel, comprises:

pumping, and preferably substantially continuously pumping, a first solution comprising a target protein, polypeptide, antibody or antibody molecule and a second solution comprising the iodine radiolabel, preferably iodine-131 or iodine-125, through a reaction chamber or tube in the presence of an effective amount of oxidizing agent;
allowing the oxidizing agent, the iodine radiolabel and the target protein, polypeptide, antibody or antibody molecule to react together during pumping through the reaction chamber or tube, thereby producing a radioiodinated protein, polypeptide, antibody or antibody molecule; and
collecting the radioiodinated protein, polypeptide, antibody or antibody molecule after pumping through the reaction chamber; and preferably
substantially purifying the radioiodinated protein, polypeptide, antibody or antibody so collected.

In the radioiodination of proteins, and particularly antibodies and antibody molecules, the one or more pumps are preferably activated at a predetermined flow rate to move the oxidizing agent, the target protein or antibody and the radioactive label into the reaction chamber or tube. The predetermined flow rate provides sufficient or ample time for the oxidizing agent to oxidize the radioactive label to form a reactive mixed halogen species. A "reactive mixed halogen species" is preferably a species capable of reacting with tyrosine and histidine residues of the target protein or antibody to produce a radiolabeled protein or antibody. Preferably, this occurs without substantial damage, e.g., without substantial radiolysis.

The radiolabeled protein or antibody is preferably pumped out of the reaction chamber or tube. More preferably, the radiolabeled protein or antibody is then pumped into a purification column, purified by pumping through the purification column and then collected.

In yet another series of embodiments, the present invention provides methods of making the foregoing and related apparatus or devices. An exemplary method of making an apparatus for radiolabeling a molecule comprises:

providing at least a first and second reagent vessel;
providing a reaction chamber or tube having a first end and a second end;
providing a peristaltic pump having at least a first and second channel;
providing at least a first purification unit, dispensing unit or collection vessel;
fluidly connecting the first reagent vessel to the first end of the reaction chamber or tube using a first reagent tubing;
fluidly connecting the second reagent vessel to the first end of the reaction chamber or tube using a second reagent tubing;
passing the first reagent tubing through the first channel of the peristaltic pump;
passing the second reagent tubing through the second channel of the peristaltic pump; and
fluidly connecting the second end of the reaction tube to the purification unit, dispensing unit or collection vessel.

These methods may further comprise fluidly connecting the second end of the reaction tube to an inlet of the purification unit and fluidly connecting an outlet of the purification unit to at least a first collection vessel.

If desired, at least a portion of the inner surface of the reaction chamber or tube may be coated with an oxidizing agent, such as 1,3,4,6-Tetrachloro-3α,6α-diphenylglycouril. Equally, a substrate, such as microparticles, attached to an oxidizing agent, e.g., N-chlorotoluenesulfonamide, may be placed into the reaction chamber or tube.

An apparatus or device may be made in which the peristaltic pump further includes a third channel. These methods may further comprise providing a third reagent vessel; fluidly connecting the third reagent vessel to the first end of the reaction tube using a third reagent tubing; and passing the third reagent tubing through the third channel of the peristaltic pump.

Having made any such apparatus or device within the invention, it may then be advantageously used without undue experimentation in any one or more of the methods of the invention, as disclosed herein, including equivalents that will be known to those of ordinary skill in the art in light of the present disclosure and the knowledge in the art.

BRIEF DESCRIPTION OF THE DRAWINGS

Further objects of the present invention, together with additional features contributing thereto and advantages accruing therefrom, will be apparent from the following description of certain preferred embodiments of the invention, which are shown in the accompanying drawing figures with like reference numerals indicating like components throughout, wherein:

FIG. 6 is a representation of a microparticle having attached thereto an N-chlorobenzenesulfonamide group (Iodo-beads);

FIG. 7 depicts labeling reactions catalyzed by sulfonamide groups attached to the bead or microparticle illustrated in FIG. 6, which forms a highly reactive iodosulfonamide intermediate that iodinates tyrosine and histidine residues in proteins;

DESCRIPTION OF ILLUSTRATIVE EMBODIMENTS

The present invention is directed to new "in-line" labeling methods and apparatus, which allow rapid, large scale production of radiolabeled therapeutic proteins and antibody doses of high quality. Each of these aspects of the present invention is discussed below in further detail.

A. Catalysts for Use in Iodination of Proteins

Figure 1:
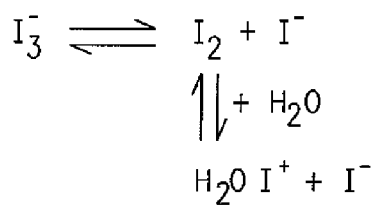
FIG. 1 depicts an iodide anion in an aqueous solution undergoing an equilibrium reaction to form a reactive $H_2OI^+$ species.
Figure 3:
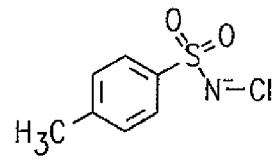
FIG. 3 is an illustration of the molecular structure of N-chlorotoluenesulfonamide (chloramine-T)
Figure 4:
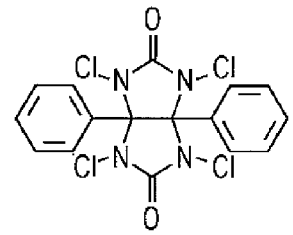
FIG. 4 is an illustration of the molecular structure of 1,3,4,6-Tetrachloro-3α,6α-diphenylglycouril (Iodogen)
Figure 2:
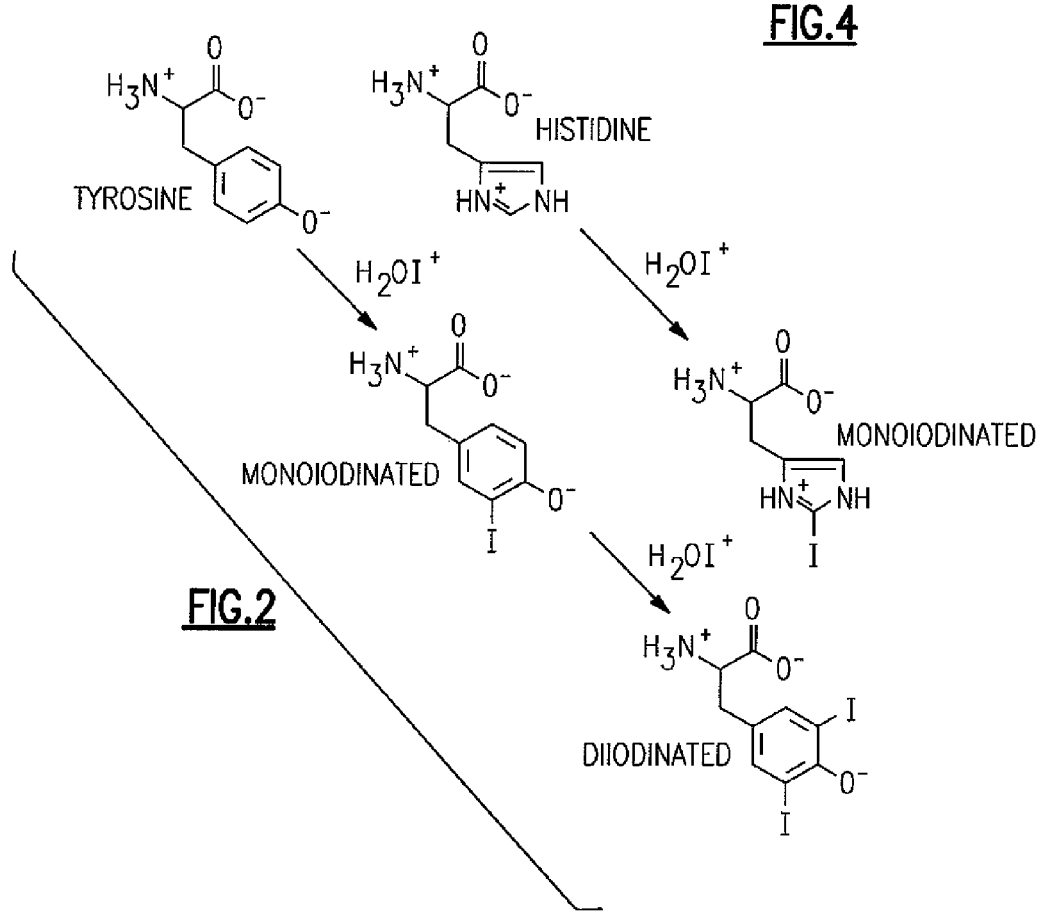
FIG. 2 shows the iodination of tyrosine and histidine residues in proteins by $H_2OI^+$.

Radioiodination is the process of chemically modifying a molecule to contain one or more atoms of radioactive Iodine. Early studies on protein modification determined that iodine in an aqueous solution forms a reactive ion $H_2OI^+$, as depicted in FIG. 1. The reactive iodine ion ($I^+$) is capable of modifying tyrosine side chains and the imidazole groups of histidine, and either modifying side groups or catalyzing their oxidation to disulfides as illustrated in FIG. 2. In addition to tyrosine (which gives the most stable iodinated product) and histidine, the indole group of tryptophan can also be labelled. More efficient methods of radioiodination utilize a chemical agent to create the reactive iodine species. The prevailing procedures for coupling radioactive Iodine, such as $^{131}I$ and $^{125}I$, to a protein is through use of an oxidizing agent including, but not limited to, N-haloamine derivatives like N-chlorotoluenesulfonamide (chloramine-T) and 1,3,4,6-Tetrachloro-3α,6α-diphenylglycouril (Iodogen). The chemical structures of chloramine-T (C-T) and Iodogen are respectively illustrated in FIG. 3 and FIG. 4.

Figure 5:
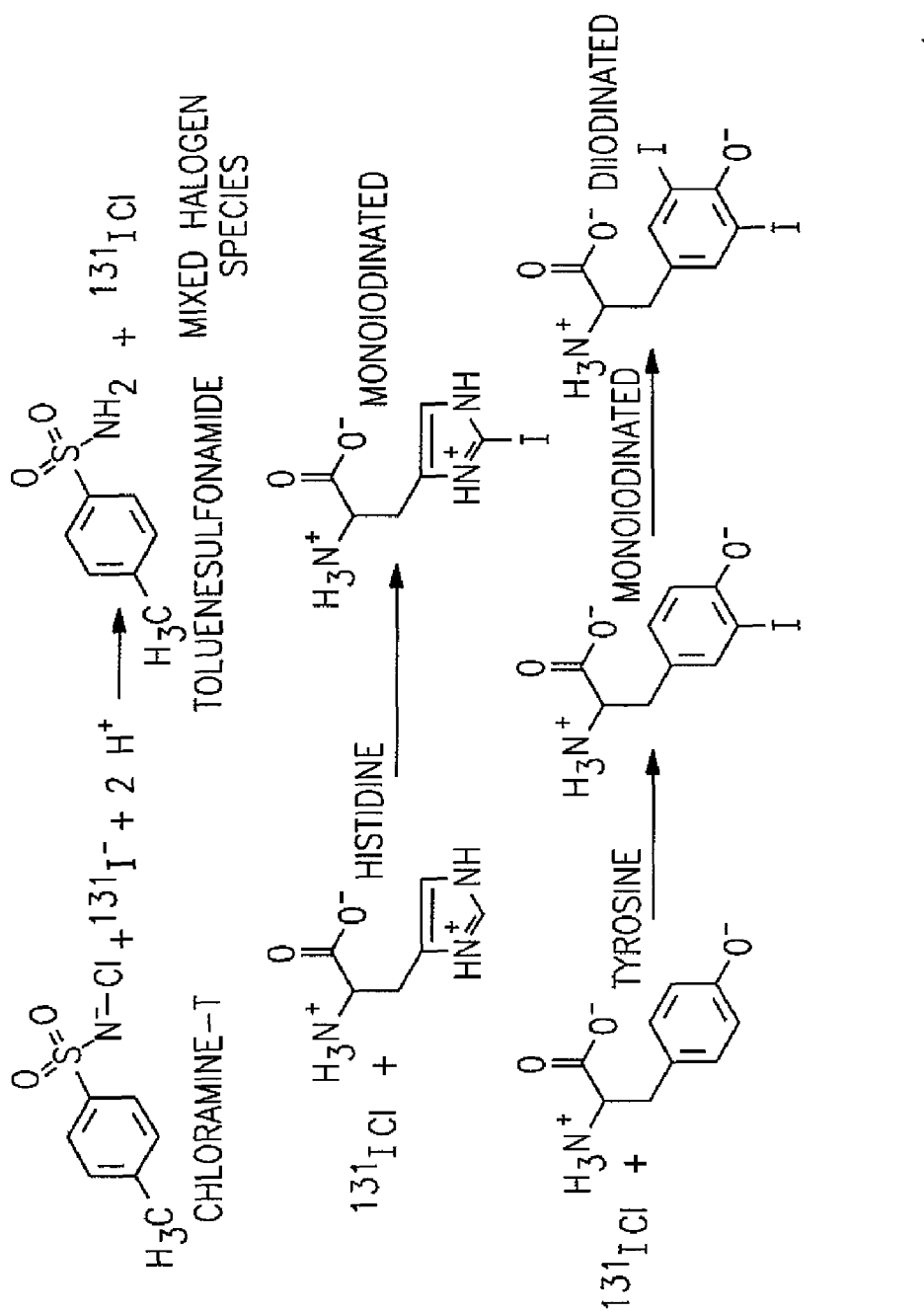
FIG. 5 illustrates the formation of a highly reactive mixed halogen species catalyzed by chloramine-T and the modification of histidine and tyrosine by the reactive halogen species.

The highly reactive halogen species rapidly reacts with compounds or substances with aromatic ring structures having substituents that are electron donating that can sufficiently activate the carbons on the ring to undergo electrophilic substitution reactions. Thus, phenols, aniline derivatives, or alkyl anilines that contain OH, $NH_2$, or NHR constituents, respectively, are very susceptible to being iodinated. Hence, in proteins, tyrosine side-chain phenolic groups and histidine side-chain imidazole groups are susceptible to iodination, as illustrated in FIG. 5. Tryptophan residues in proteins can also be labelled via their indole group.

It is know in the art that addition of a radioactive iodine atom to a protein molecule typically has little effect on its protein activity unless its active site is modified in the process. In addition, iodine is a relatively small molecule and does not cause steric hindrance problems. As mentioned above, the site of modification is tyrosine and histidine side chains, and also tryptophan. Tyrosine may be modified with a total of two iodine atoms per phenolate group, whereas histidine can incorporate one iodine, as shown in FIG. 5.

The reaction of chloramine-T with iodide in solution results in oxidation with subsequent formation of the reactive, mixed halogen species, ICl (FIG. 5). The ICl then rapidly reacts with any sites within target molecules that can undergo electrophilic substitution reactions as discussed above. Since chloramine-T is soluble in aqueous solutions, the reaction is carried out completely in the solution phase, which results in higher incorporation of radioactive iodine than using insoluble or immobilized oxidants such as Iodogen or Iodobeads, respectively, as described below.

With reference now to FIG. 6, there is shown an example of an immobilized chloramine-T analog. As illustrated, a polystyrene microparticle or bead has been derivatized to contain a N-chlorobenzenesulfonamide group. Unlike water soluble oxidants, the oxidizing ability of immobilized oxidants is limited to the surface of its solid support, which significantly reduces the rate of iodine incorporation into macromolecules. This may be advantageous if a slow rate and low incorporation is desired. One may also limit iodination of tyrosine to mono-iodo forms, thus avoiding detrimental effects on solubility or activity that excessive modification can cause.

Referring next to FIG. 7, there is illustrated another mechanisms of iodination of tyrosine and histidine using the derivatized microparticle of FIG. 6. In contrast to the mechanism using chloramine-T, shown in FIG. 5, a reactive mixed halogen species is not formed in this reaction. Instead, the sulfonamide group forms a highly reactive iodosulfonamide intermediate that iodinates tyrosine and histidine residues in proteins as shown.

Figure 8:
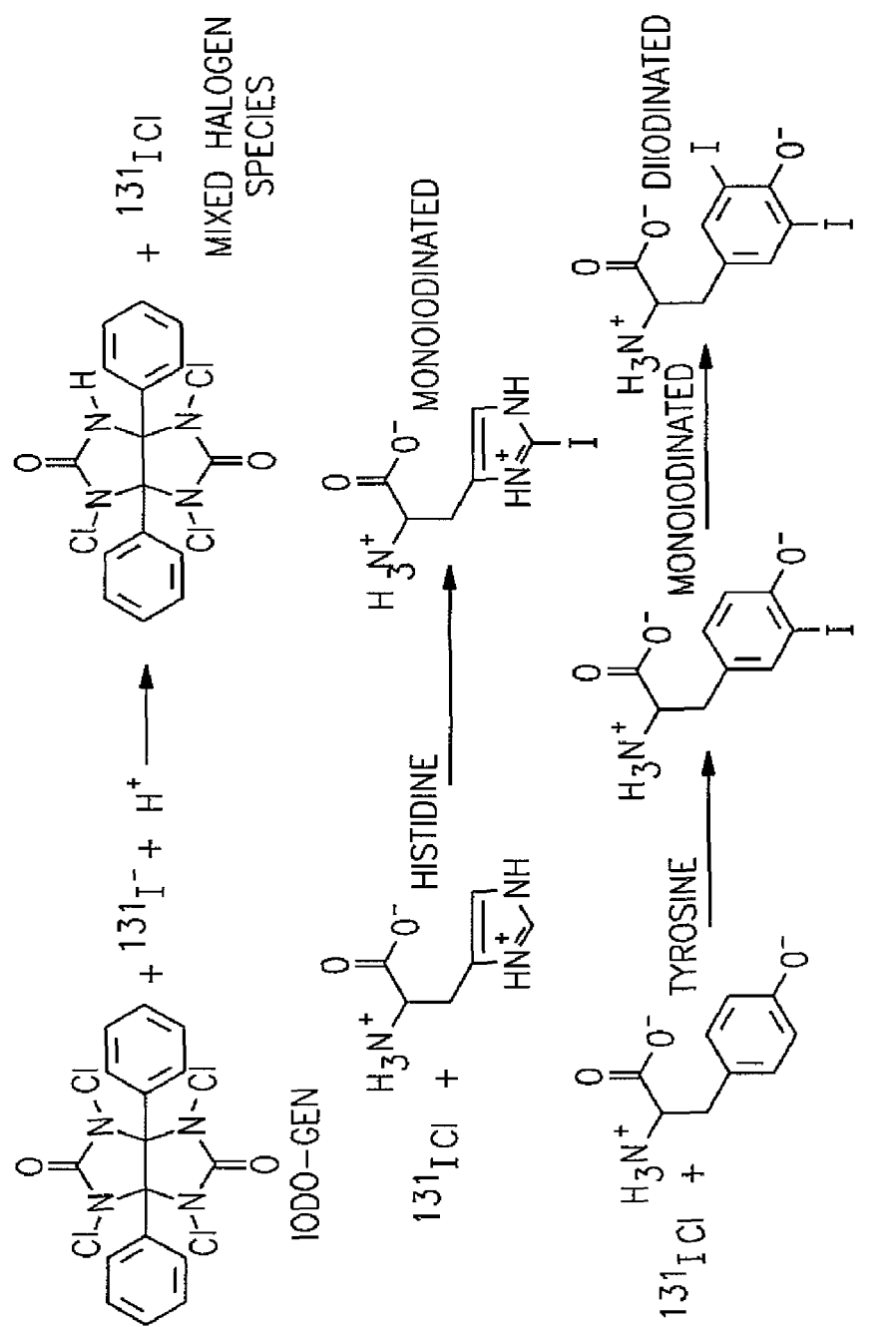
FIG. 8 illustrates the formation of a highly reactive mixed halogen species catalyzed by Iodogen and the modification of histidine and tyrosine by the reactive halogen species.

The next figure, FIG. 8, shows yet another method for forming the mixed halogen species using the insoluble oxidant Iodogen. Since Iodogen is insoluble in an aqueous solution, it is used as a solid-type radioiodination reagent. Unlike Iodobeads, wherein the oxidizing group is covalently immobilized on a solid support, Iodogen is plated out on a solid support or reaction vessel prior to iodination. Similar to that with chloramine-T, the reaction of Iodogen with iodide in solution results in the formation of the reactive mixed halogen species ICl, as illustrated. The ICl then rapidly reacts with target molecules that can undergo electrophilic substitution reactions as discussed above.

B. Continuous In-Line Radiolabeling

As mentioned above, the present invention relates to continuous, in-line, mobile phase radiolabeling of proteins within a reaction tube or vessel using a controlled flow of reactants resulting in a highly efficient, large-scale radiolabeling method. Although a surprising advance, the present invention is flexible to use in a variety of embodiments, e.g., as described below in conjunction with FIGS. 9 to 15.

Figure 9:
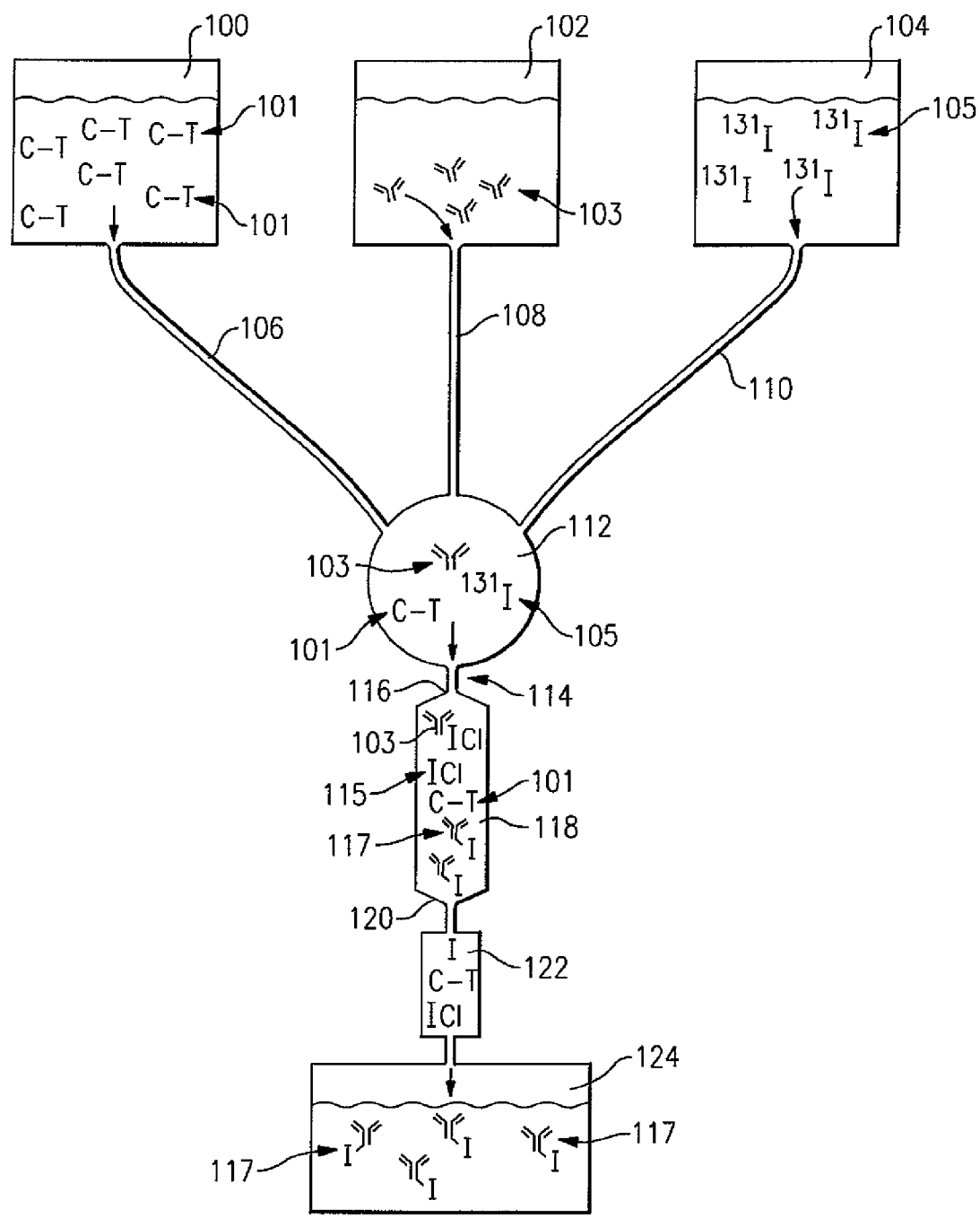
FIG. 9 is a schematic illustration of an embodiment of an apparatus and method of the present invention for radiolabeling proteins with $I^{131}$.

Referring specifically to FIG. 9, there is shown an embodiment of the apparatus and method of the present invention for radiolabeling an antibody. The apparatus may include a first reagent vessel 100, a second reagent vessel 102 and a third reagent vessel 104, the reagent vessels are fluidly connected to a mixing chamber 114, respectively though a first reagent tubing 106, a second reagent tubing 108 and a third reagent tubing 110. Each of the reagent tubings passes through a pump 112 before merging into the mixing chamber 114. Pump 112 is preferably a controllable multi-channel peristaltic pump such as, for example pumps used in liquid chromatography. Mixing chamber 114 is fluidly connected to a first end 116 of a reaction tubing or vessel 118. A second end 120 of reaction tubing 118 is fluidly connected to a purification chamber or column 122.

Purification column 122 contains capture agents that bind to unattached or free radioactive elements and reaction reagents, but allow the labeled protein to pass through. Purification column 122 may contain an anion resin and or chloromethylated polystyrene or substances well known in the art that capture oxidized iodide and free iodine. The labeled proteins are then collected in a collection vessel 124. The system can be adapted from a very small range to a very large scale with practically no limits by varying the diameter of the tubing and using an appropriate peristaltic pump. The rate of the reaction and amount of labeling may also be controlled by varying the flow rate of the solution and varying the length and/or diameter of the reaction tubing 118. Hence, those of ordinary skill in the art will, in light of the present disclosure, understand that the combinations can be varied effectively.

For example, any possible diameter of reagent tubing may be used, generally depending on the size of the batch to be produced. If the amount of the cold protein or antibody is large, a larger diameter reagent tubing for the antibody and smaller diameter reagent tubes for the oxidant and radioactive label are preferred. The reaction time can also be regulated with the speed (flow) of the pump, as well as with the length of the reaction tubing. Thus, the invention does not have any significant limits. In light of the present disclosure, it is now possible to produce a single dose with narrow or thin reaction tubings and several hundreds of doses with reaction tubes of larger diameters.

Important differences and advantages of the present invention over the prior art methods of batch labeling include that there is only a small part of the activity under the reaction conditions and the ability to label almost unlimited amounts of protein or antibody in a short production time. Prior to the present invention, it was not possible to label many doses in a single batch because high radioactivity in large volume batches damages antibodies, such that the labeling reaction does not take place. All such drawbacks are overcome by the present invention.

FIG. 9 also shows the reagent vessels filled with various reagent solutions. Vessel 100 is filled with a water soluble oxidizing agent such as chloramine-T (C-T) 101, vessel 102 is filled with antibodies 103 to be labeled, and vessel 104 is filled with $^{131}$I 105. When pump 112 is started, the reagents are then pumped from the reagent vessels into their respective reagent tubings into the mixing chamber 114 where each of the reagents is mixed. The mixed solution then enters the reaction tubing where C-T 101 reacts with the $^{131}$I 105 to form the reactive mixed hydrogen species ICl 115, which reacts with the tyrosine and histidine side chains of the antibody 103 to thereby label the antibody with $^{131}$I as described above in conjunction with FIG. 5. The mixed solution is allowed to move through the reaction tubing 118 for a predetermined time enough to label most, if not all, of the antibodies in the mixed solution. As one of skill in the art will appreciate, this labeling process can continue indefinitely thus providing a high volume of labeled product. After the mixed solution, now containing labeled product 117, passes through the reaction tubing 118, it enters the purification column 122 where any remaining free $^{131}$I 105, halogen species 115 and C-T 101 are removed from the solution. The purification column allows the labeled antibody product 117 and any unlabeled antibody 103 to pass through, which is collected in the collection vessel 124, as shown in FIG. 9.

Figure 10:
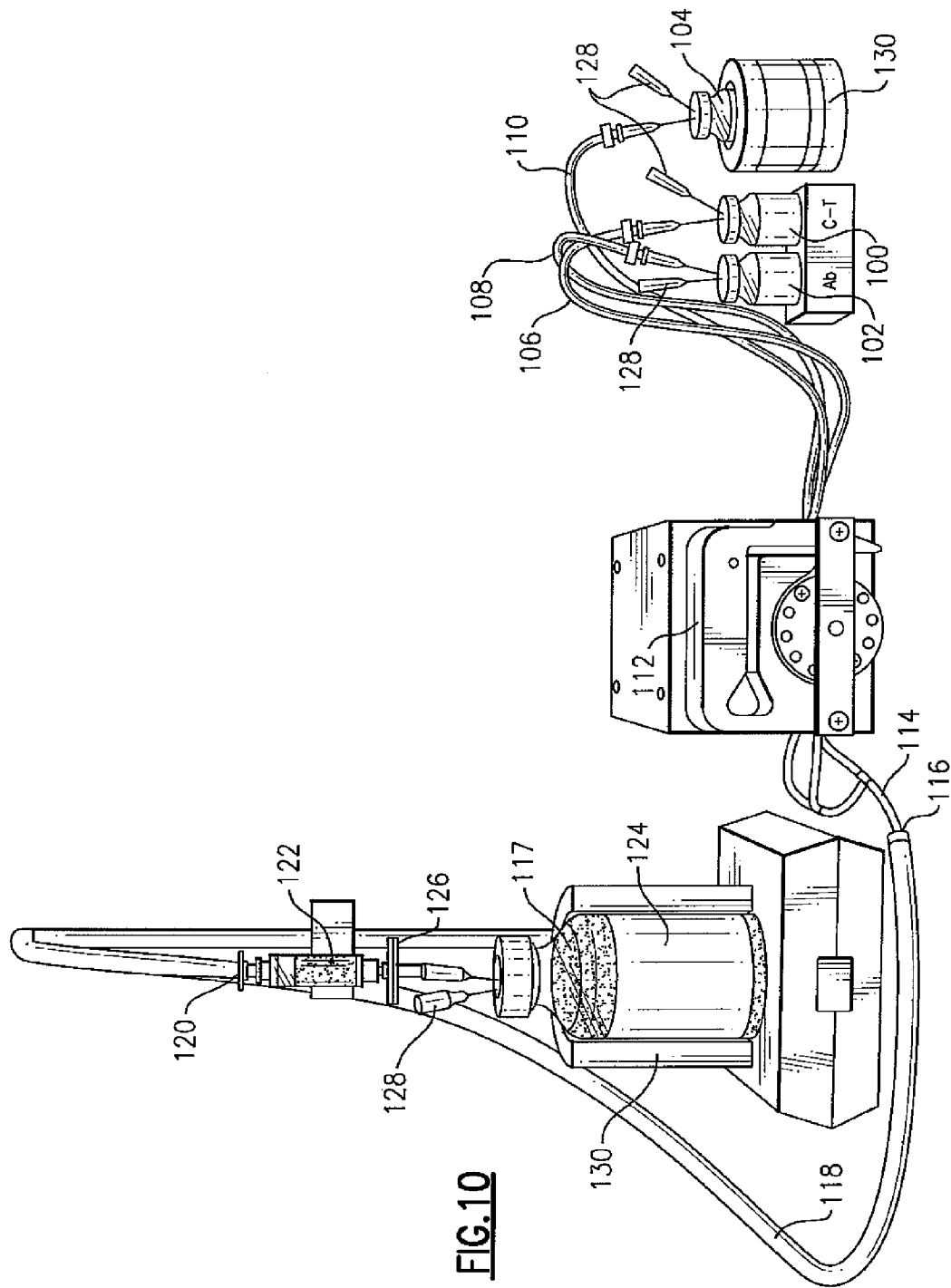
FIG. 10 is a pictorial representation of an exemplary apparatus and methodology of the present invention.

Referring next to FIG. 10, there is shown a pictorial representation of the apparatus of FIG. 9 having all the described components and further including vent ports 128 to prevent the formation of pressure and or vacuum within the vessels and tubings of the apparatus. Lead shields 130 are also shown surrounding vessel 104 containing radioactive iodine and the collection vessel 124 containing the radiolabeled antibody 117. An optional in-line filter 126 to filter the solution coming out of the purification column 122 prior may also be added to the apparatus as shown. The in-line filter is preferably a sterile filter.

Figure 11:
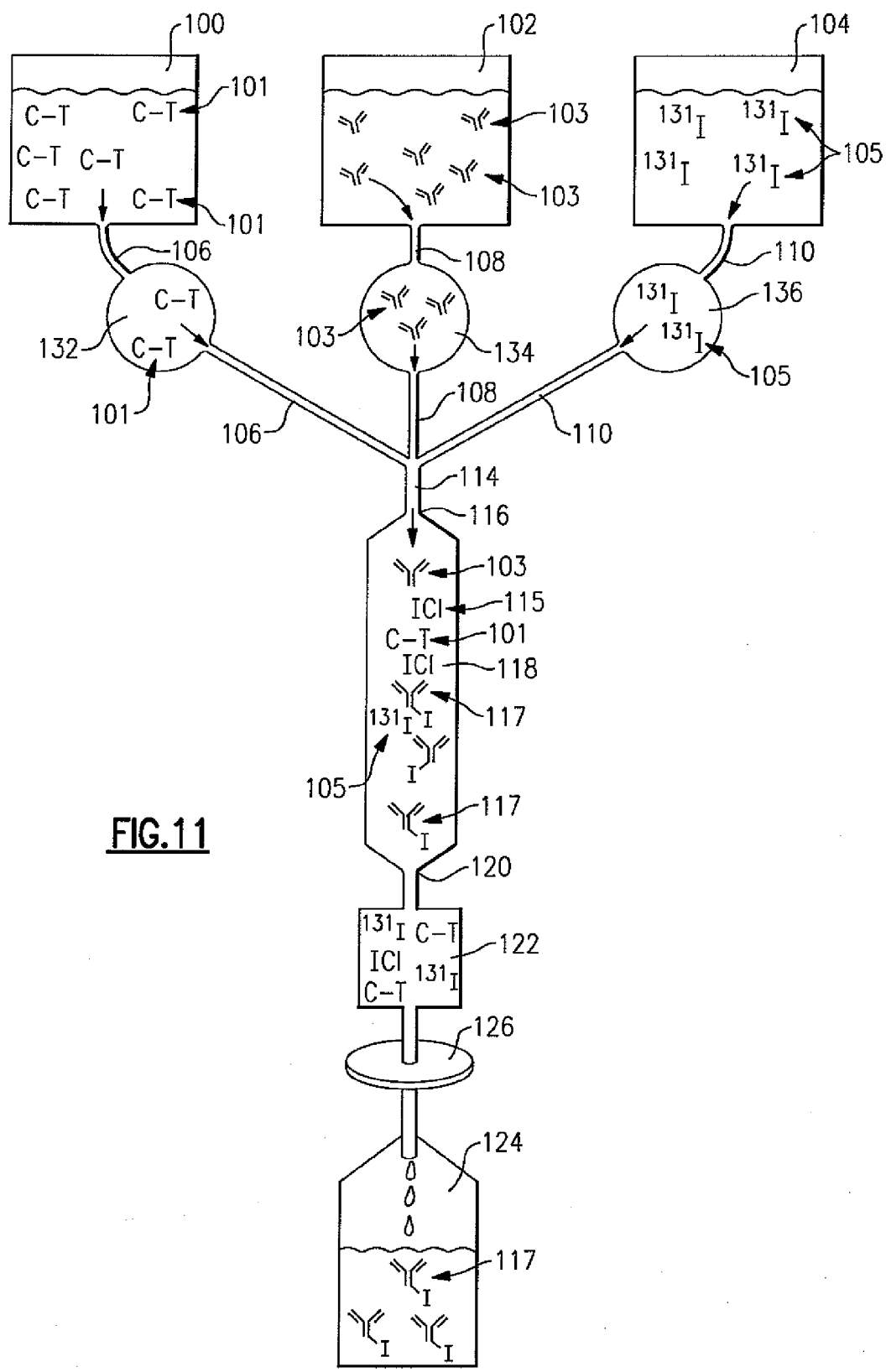
FIG. 11 is a diagrammatic representation of another embodiment of the apparatus and method for radiolabeling of the present invention.

Referring now to FIG. 11, there is illustrated another embodiment of the apparatus described in conjunction with FIG. 9 and FIG. 10. In this embodiment, reagent tubings 106, 108 and 110 from each of the respective reagent vessels 100, 102 and 104 pass through individual peristaltic pumps. Wherein, tubing 106 passes through a first pump 132, tubing 108 passes through a second pump 134, and tubing 110 passes through a third pump 136. The reagent tubings then converge into the mixing chamber 114, which is fluidly connected to the first end 116 of the reaction tubing 118. The second end of the reaction tubing 118 is in fluid communication with the purification column 122. The purification column is then fluidly connected to an incline filter 126. The output from filter 126 is collected in the collection vessel 124.

A particular advantage of using separate pumps for each of the reagent vessels is that the flow rate from each pump can be controlled separately. This allows for the optimization and control of the amount of labeling of each of the target proteins or antibodies in solution. As a non-limiting example, monoiodination of tyrosine can be achieved by setting the flow rate of pumps 132 and 136 slow, relative to the flow rate of pump 134, thus allowing more antibody and less oxidant and reactant in the resulting mixture thereby decreasing the chances of diiodination of tyrosine residues in the protein. The ratio between each of the reactants can thus be controlled by varying the flow rate of each pump. One of skill in the art will thus appreciate the versatility of this set-up.

Figure 12:
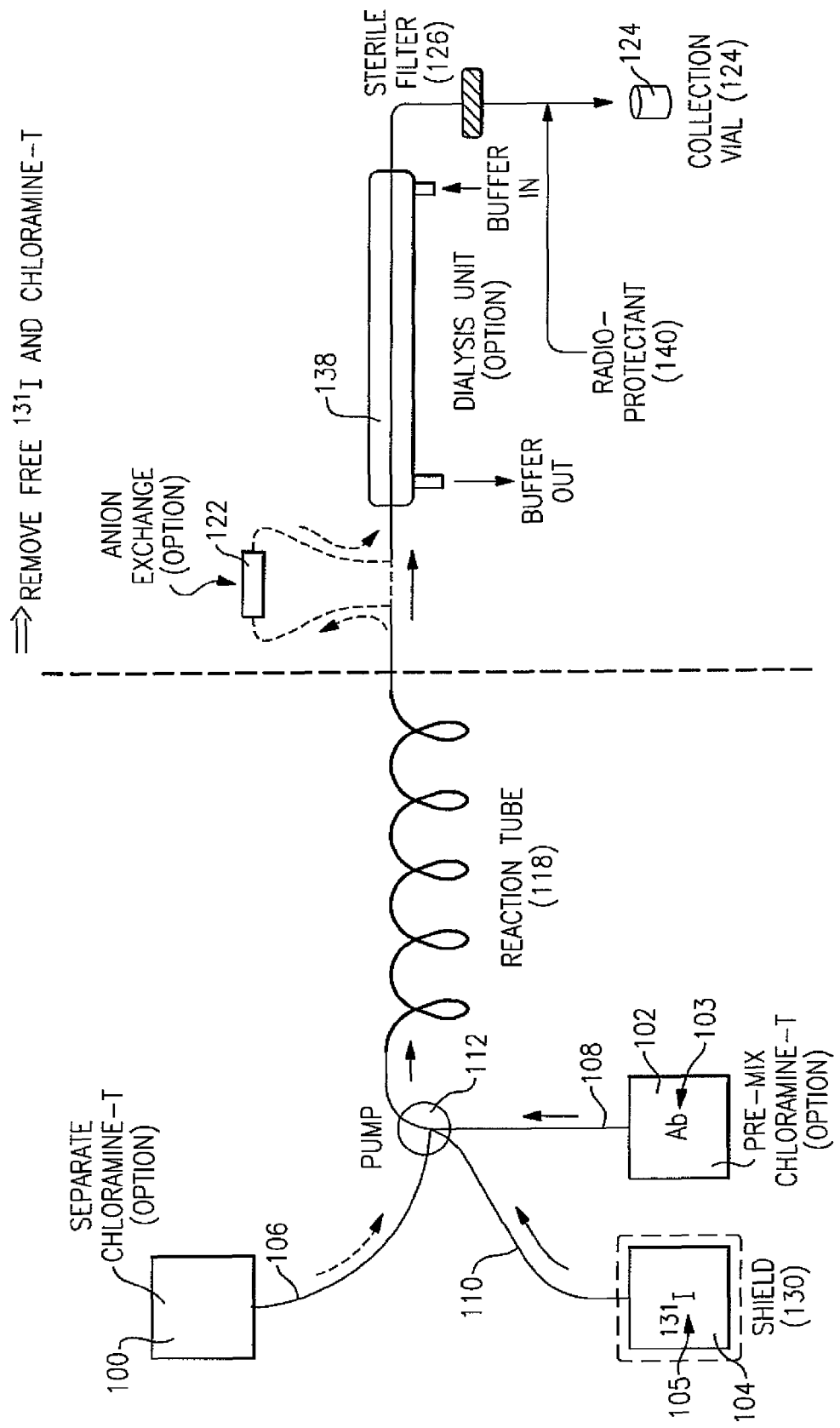
FIG. 12 is a schematic diagram of different embodiments of the present invention.

With reference now to FIG. 12, there is shown a schematic diagram illustrating different alternate embodiments of the apparatus of the present invention. One embodiment, also described above in conjunction with FIG. 9 and FIG. 10, includes three reagent vessels 100, 102 and 104, a multi-channel peristaltic pump 112, a reaction tube 118, a purification column 122 and a collection vessel 124. In another embodiment, a particulate or sterile filter 126 is placed between purification column 122 and collection vial 126, as illustrated. In yet another embodiment, a dialysis unit 138 instead of a purification column 122 is used to purify the radiolabeled product. A radioprotectant 140 is preferably added to the final radiolabeled product 117 to prevent damage to the product from radiation. Radioprotectant may include, but is not limited to, for example, serum albumins, such as human serum albumin, bovine serum albumin, horse serum albumin and serum albumins from other mammalian species; sodium ascorbate; and other substances that absorb radiation and do not interact with the radiolabeled product.

In still another embodiment of the present invention, only two reagent vessels 102 and 104 are used instead of three. In this embodiment, the oxidizing agent is mixed with the molecule, protein or antibody to be labeled 103 in vessel 102 and the radioisotope label $^{131}$I 105 is placed in vessel 104. Both of these solutions are then pumped through reaction tube 118 using pump 112 at a predetermined flow rate enough to allow ample time for labeling antibody 103. As discussed above, the solution eluting out of tube 118 is then purified to remove free radioactive iodine 105, the oxidizing agent 101 and any reactive intermediates 115 using purification column 122. Column 122 is preferably an anion exchange column. Alternatively, a dialysis unit 138 may be used to purify the product, or both column 122 and dialysis unit 138 may be used to purify the product.

Figure 13:
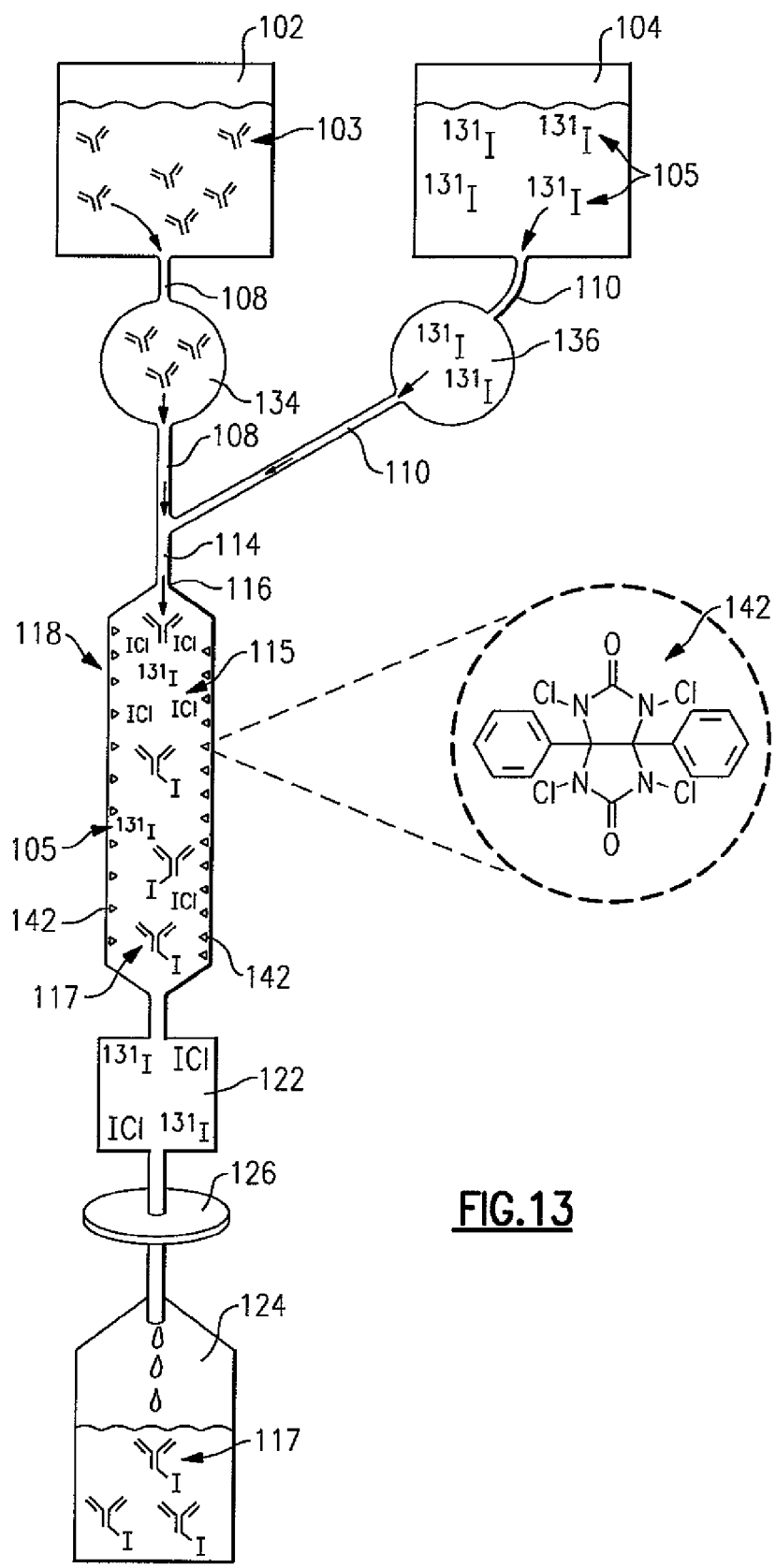
FIG. 13 is an illustration of a further embodiment of the apparatus and method of the present invention for radiolabeling proteins using a reaction vessel coated with Iodogen.

The next figure, FIG. 13, depicts yet another alternate embodiment of the present invention. In this embodiment, two reagent vessels 102 and 104 are used. Each vessel is fluidly connected to mixing chamber 114 through respective reagent tubings 108 and 110. Tubing 108 and 110 pass through respective peristaltic pumps 134 and 136. Mixing chamber 114 is fluidly attached to the first end of reaction chamber 118. Reaction chamber 118 is coated with a non-water soluble oxidizing agent 142. Oxidizing agent 142 is preferably Iodogen, as depicted. The second end 120 of reaction chamber 118 is fluidly connected to purification column 122, which is fluidly connected to filter 126. The output from filter 126 is collected in collection vial 124. As described above, in conjunction with FIG. 8, the radioactive label $^{131}$I 105 is oxidized by Iodogen to form the reactive mixed halogen species ICl 115. The flow rate of pumps 134 and 136 is set at a pre-determined rate to provide desired amounts or ratio of antibody 103 and radioiodide 105 for labeling. The mixture of antibody 103 and radioiodide 105 is allowed to pass through reaction chamber 118 for a predetermined time to maximize the labeling of antibody 103. This is achieved by setting the flow rate accordingly.

Figure 14:
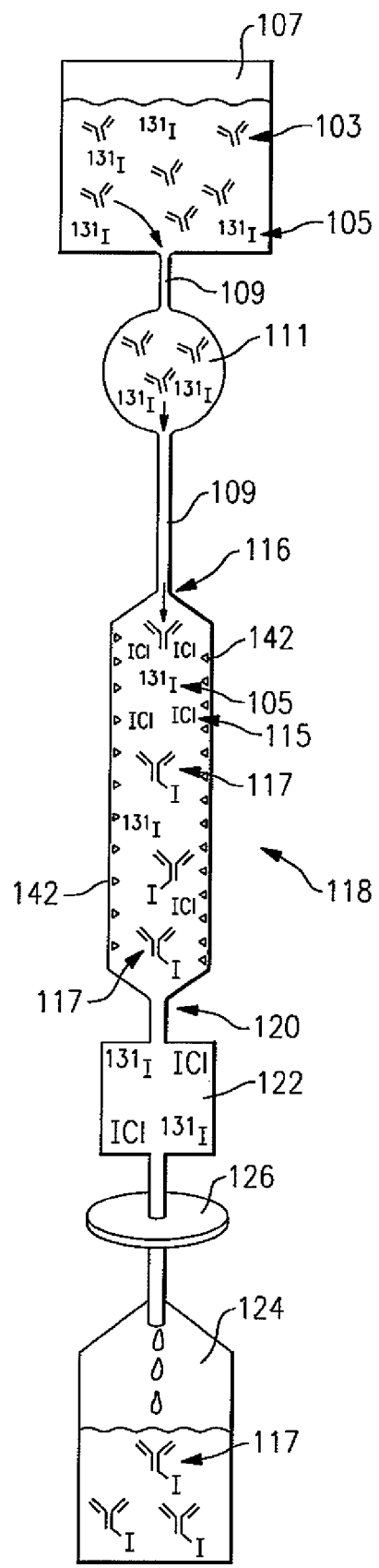
FIG. 14 is an illustration of still another embodiment of the apparatus and method of the present invention for radiolabeling proteins using a reaction vessel coated with Iodogen.

Moving on to FIG. 14, there is represented another embodiment of the apparatus and method of FIG. 13. This embodiment includes a single vessel 107 fluidly connected to the first end 116 of reaction chamber 118 through tube 109. Tube 109 passes through peristaltic pump 111. Reaction chamber 118 is fluidly connected at its second end 120 to purification filter 122, which is fluidly connected to filter 126. The resulting purified and filtered product 117 is gathered in collection vessel 124. As illustrated, the antibody 103 and radioactive label 105 are placed in vessel 107. This mixture is then pumped through tubing 109 using pump 111 at a predetermined rate to allow ample time for the oxidizing agent 142 on the walls of chamber 118 to react with label 105 to produce halogen species 115. Halogen species 115 then covalently binds with the tyrosine and histidine residues on antibody 117, as described above to produce the radioactively labeled product 117.

Figure 15:
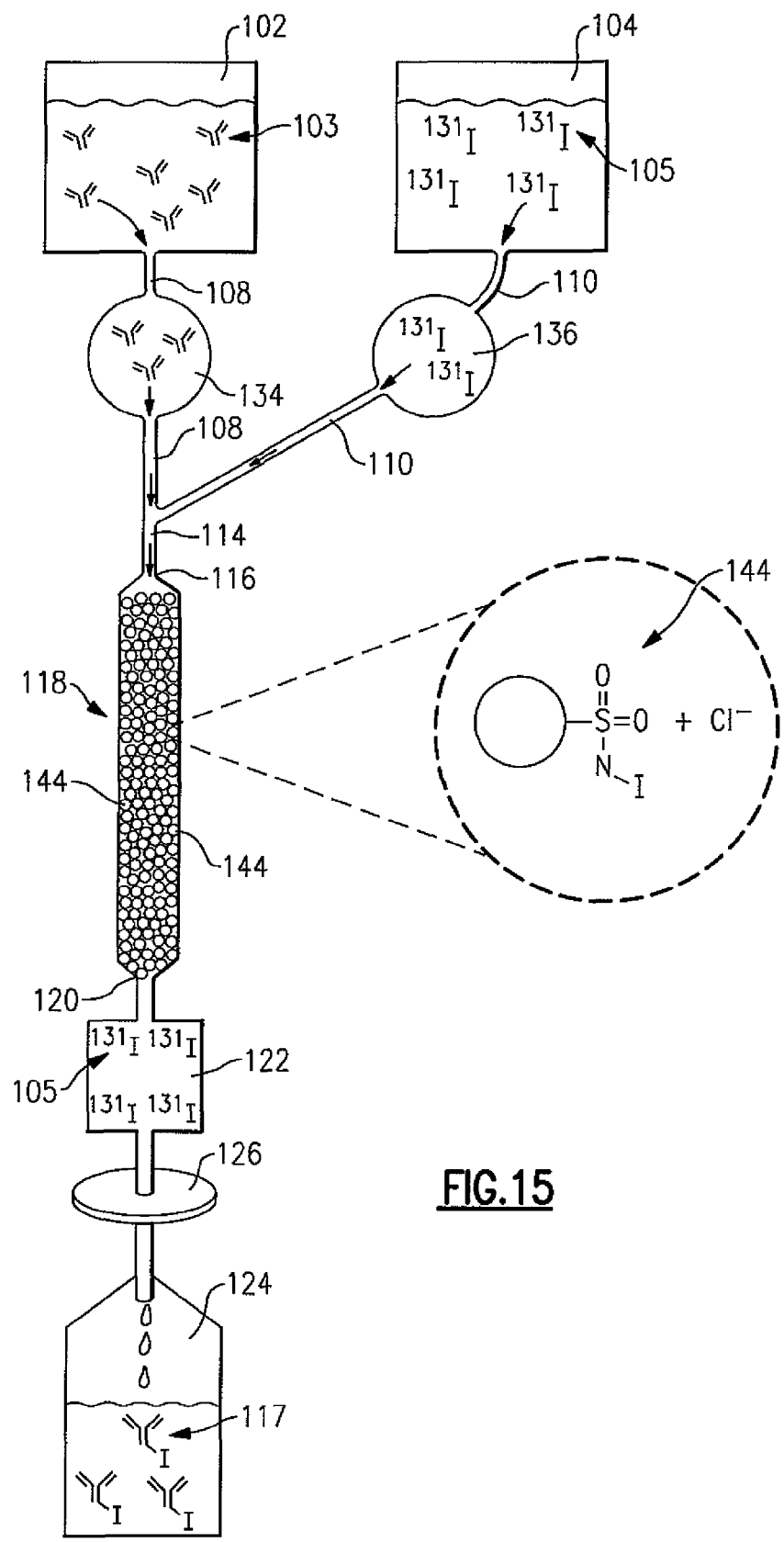
FIG. 15 is an illustration of yet another embodiment of the apparatus and method of the present invention for radiolabeling proteins using a reaction column filled with Iodobeads.

Referring next to FIG. 15, there is illustrated still another alternate embodiment of the apparatus and methods of the present invention. In contrast to the embodiment described above in conjunction with FIG. 13 and FIG. 14, reaction chamber 118 is filled with microparticles 144 having attached thereto an oxidizing agent as shown. Reagent vessels 102 and 104 are fluidly connected to the mixing chamber 114 through respective reagent tubings 108 and 110. Mixing chamber 114 is fluidly connected to the fist end 116 of chamber 118. The second end of chamber 118 is fluidly connected a purification chamber 122, which is in fluid communication with filter 126. The purified product 117 is collected in vessel 124 as shown. In use, vessel 102 is filled, for example, with cold antibodies while vessel 104 is filled with radioactive iodine 105. Pump 134 and 136 are then activated to pump the solutions in vessels 102 and 104 into mixing chamber 114 at a predetermined flow rate to achieve a desired ratio of antibody 103 and radioactive label 105. The solutions then mix within the mixing chamber 114 before entering reaction chamber 116. Once in the chamber 116, the oxidizing agents attached to the microparticles 144 react with the radioactive iodine 105 in the solution to form a highly reactive iodosulfonamide intermediate that iodinates tyrosine and histidine residues in proteins as described above in conjunction with FIG. 7. Any remaining free radioactive iodine 105 is then filtered out of the solution in the purification chamber 122. The purified solution then passes through filter 126 to remove large particulates in solution. The purified filtered solution containing the radiolabeled antibody 117 is then collected in vessel 124.

C. Continuous Large Scale Protein Labeling

The disclosure of the present invention shows that the goal of developing a large scale radiolabeling method designed for the pharmaceutical industry has been realized. The methods of the present invention, as described above and in the Examples below, are able to radiolabel proteins with several GBq in a short production time, and are thus widely applicable to producing a range of diagnostic and therapeutic radiopharmaceuticals.

Prior to the present invention, several parameters limited the large scale labeling of proteins, including antibodies. Important limiting factors were the total activity, the volume of the labeling batch and the radiolysis of the product. For example, in methods of the prior art, the protein to be labeled and the radiolabel were incubated in a single vessel, so that all the radiolabel was in contact with the protein for the entire reaction process. Moreover, the radiolabel remained in contact with the protein for the extra time that was needed for purification. Over the typical reaction and purification times, this had the drawback of causing protein denaturation and aggregation. Furthermore, the individuals operating such batch mode labeling techniques needed to be shielded throughout the process, typically requiring 4-6 inches of lead shield. In addition to such difficulties, the specific activity of the products produced by the prior art and existing methods are limited; the processes are expensive and not amenable to scale up.

The new approach of the present invention avoids these difficulties by labeling the batch of material in a continuous manner, with only a small portion of the protein and radiolabel in contact at any given time, as described above in conjunction with FIGS. 9, 10, 11, 12, 13 and 15. Although suitable for use with any radiolabel, the present invention is particularly advantageous for use with Iodine-131. For example, in contrast to labeling with agents such as technetium and yttrium, labeling with Iodine-131 is more problematic using the prior art methodology, particularly for embodiments other than small scale labeling. When attempting large scale labeling with Iodine-131, radiolysis is a very significant problem, which damages the protein or antibody and limits the usefulness of these techniques.

The present invention overcomes various drawbacks in current radiolabeling techniques, particularly those for labeling with Iodine-131. Rather than being incubated solely in "batch mode", the biological component, protein or antibody to be labeled is contacted with the Iodine-131 activity and oxidation agent in "continuous mode", so that only a small portion of the protein, Iodine-131 activity and oxidation agent are mixed together at any given time, as mentioned earlier. The oxidation agent, such as chloramine-T or Iodogen oxidizes the Iodine-131, which then reacts with groups on the biological component to be labeled, such as with tyrosine on proteins and antibodies, as discussed above in conjunction with FIGS. 1 to 8.

The labeling apparatus or device of the invention can differ in size, but generally comprises three different processing segments. These are shown in the schematic of FIG. 9 and also in the photographic illustration of FIG. 10. Referring again to FIG. 9 and FIG. 10, the first segment of the process utilizes three separate reaction component reservoirs 100, 102 and 104 containing reagents, educts or reactants: protein 103, chloramine-T 101 and Iodine-131 105 in a local lead shielding 130 (FIG. 10). The second segment comprises tubing 106, 108 and 110 that leads from each respective reagent reservoir 100, 102 and 104 through pump 112, preferably a three channel peristaltic pump, into a single mixing tube 114 then into the reaction chamber or tube 118 where the labeling reaction takes place. The third segment of the process concerns inline purification comprising an inline purification unit 122 and collection device 124. Various purification devices are suitable, such as size exclusion columns, anion exchange columns, ion exchange columns and dialysis means, as described above in conjunction with FIG. 11. The purification unit or device 122 is preferably followed by a sterile filter 126 and a collection vial 124. The collection vial preferably contains additives and stabilizers such as a radioprotectant for use in the final product.

Although the embodiment of the invention depicted in FIG. 9 and FIG. 10 uses three separate reaction component reservoirs, the protein and chloramine-T may be combined within a first component reservoir and the Iodine-131 solution maintained in a second component reservoir with local lead shielding as depicted in FIG. 12. Thus, the invention provides for a two reservoir system, which can utilize a two channel peristaltic pump. In other embodiments, non-water soluble components, such as Iodogen, may be used rather than chloramine-T as described above in conjunction with FIG. 13 and FIG. 14. Iodogen may be dissolved in chloroform and used to coat the reaction tube 118. Iodogen may also be used in the form of beads, such as Iodobeads, which are essentially chloramine-T bonded to a bead.

In any mode, the entire labeling device or apparatus with sterile disposable components can be prepared under aseptic conditions in a shielded labeling hood and finally, to minimize the radiation burden of the personnel, the vial containing the Iodine-131 solution can be connected to the device.

In the operation of the labeling apparatus and methods of the present invention, the educts or reactants from the reagent reservoirs, whether two or three reservoirs, lead into the reaction tube or vessel, preferably using a peristaltic pump. Therefore, the reaction components are mixed only just before entering into the reaction tube. It is also straightforward to regulate the reaction time using the present invention, e.g., by varying the length and/or diameter of the reaction tube, as well as by varying the flow rate of the pump.

The labeling reaction is stopped, without adding any reduction agent, simply by removing the free iodine and the oxidant. These agents are removed from the process by in-line purification, such as by using an in-line purification column 122 mounted at the end of the reaction tube 118. The labeled protein or antibody solution is collected in vial(s), preferably already containing stabilizers, radioprotectants, e.g., ascorbate or inert proteins such as BSA, and/or any additives desired for the final formulation. This allows the labeled product to be diluted to the chosen level in the collecting system or vial, for example, to dispense radiolabeled proteins or antibodies into single doses and quality control samples. The method can be run for an extended period of time, for example, in a manner effective to dispense labeled proteins into 10,000 or more vials for patient treatment.

The following examples are included to demonstrate certain preferred embodiments of the invention. It will be appreciated by those of skill in the art that the methods, apparatus and compositions disclosed in the examples that follow represent methods, apparatus and compositions discovered by the inventors to function well in the practice of the invention, and thus can be considered to constitute preferred modes for its practice. However, those of skill in the art will, in light of the present disclosure, appreciate that many changes can be made in the specific embodiments that are disclosed and still obtain a like, similar or equivalent result without departing from the spirit and scope of the invention, as embodied in the appended claims.

EXAMPLE 1

Continuous, Large Scale In-Line Radiolabeling of Proteins

The present and subsequent examples describe the successful development of a large scale radiolabeling method and apparatus, with advantageous applications in the pharmaceutical industry.

The inventors have used an apparatus and method of the invention, particularly the apparatus and method described above in conjunction with FIG. 9 and FIG. 10, to radiolabel batch sizes up to 487 GBq of $^{131}$I bound to a monoclonal antibody (Table 1). The entire processing took approximately 40 minutes including reaction time, purification and final formulation. Free Iodine varied between 0.1 and 2.1%. The overall yield was at minimum 85%, with a maximum of 96%. Size exclusion chromatography analyses were performed on each batch of labeled antibodies, which showed negligible fragmentation and aggregation of the antibody and above 95% intact radiolabeled antibody monomer. Exemplary results of the large scale production are presented in Table 1. Cell binding potency assays were conducted to demonstrate the high quality of the product, which showed over 80% potency relative to unlabeled antibodies from the same production lot.

TABLE 1

| Batch | Activity GBq | Chloramine-T Mg | Antibody mg | Total Vol. mL | Reaction Time Min. | Yield GBq | Yield % | Free Iodine % |
|---|---|---|---|---|---|---|---|---|
| A | 47.9 | 1.8 | 60 | 3 × 3.3 | 10 | 42.9 | 90 | 1.4 |
| B | 25.2 | 0.9 | 30 | 3 × 3.3 | 10 | 21.4 | 85 | 0.1 |
| C | 288.2 | 25 | 450 | 3 × 20.0 | 10 | 256.5 | 89 | 1.8 |
| D | 487.3 | 30 | 1000 | 2 × 10 + 50 | 10 | 466.8 | 96 | 2.1 |

EXAMPLE 2

Continuous, In-Line Radiolabeling and Purification by Dialysis

This example particularly concerns the use of dialysis to purify the radiolabeled products from the large scale production methods of the invention.

In this example, the protein to be labeled is the Lym-1 antibody. Further details relating to the Lym-1 antibody and uses thereof are provided in U.S. Pat. No. 4,724,213, entitled "Murine Hybridoma Lym-1 and Diagnostic Antibody Produced Thereby"; U.S. Pat. No. 4,861,579, entitled "Suppression of B-lymphocytes in mammals by administration of anti-B-lymphocyte antibodies"; U.S. Pat. No. 5,194,594, entitled "Modified Antibodies"; and U.S. Pat. No. 6,007,817, entitled "Vasopermeability Enhancing Conjugates"; each of which are specifically incorporated herein by reference in their entireties.

Lym-1 antibodies were labeled with I-131 using a configuration having two 4 ml reagent vessels and a dialysis purification unit, generally as described above in conjunction with FIG. 12. The first reagent vial was filled with a mixture containing 80 mCi I-131 (sodium salt), 5 mg Lym-1 in 250 ml, and 3 ml of 0.1M potassium phosphate. In the second reagent vial, 100 μl of 0.5 mg chloramine-T was mixed with 3 ml potassium phosphate. The flow rate of the peristaltic pump was set to 0.6 ml/min, while the reverse flow rate of the dialysis solution (0.9% NaCl) was set to 8 ml/min. The reaction time within the reaction tube for this batch was 12 minutes. The efficiency of the dialysis purification was calculated to be 99.9%. The reaction was stopped only by dialysis, without adding sodium metabisulfite. The yield or labeling efficiency for this batch was 92%.

In a second labeling batch using the same configuration, the first 4 ml reagent vial was filled with a mixture containing 71 mCi I-131 (sodium salt), 5 mg Lym-1 in 250 ml, and 3 ml of 0.1M potassium phosphate. The second 4 ml reagent vial was loaded with 100 μl of 0.5 mg chloramine-T dissolved in 3 ml potassium phosphate. The flow rate of the peristaltic pump was similarly set to 0.6 ml/min, while the reverse flow rate of the dialysis solution (0.9% NaCl) was similarly set to 8 ml/min. The reaction time within the reaction tube for this batch was 19 minutes. The yield or labeling efficiency for this batch was 88%. The potency or binding affinity (relative to the unlabeled Lym-1 antibody) of the resulting radiolabeled Lym-1 antibodies was determined to be 94%.

EXAMPLE 3

Continuous, In-Line Radiolabeling and Purification by Ion Exchange

The present example describes the use of an ion exchange column to purify radiolabeled Lym-1 antibody prepared by the methods of the invention.

Lym-1 antibodies were radiolabeled with I-131 (sodium salt) using a configuration of the invention as described above in conjunction with FIGS. 9 and 10. With reference to FIG. 10, in this labeling batch, the first reagent vial 100 was filled with 10 ml of 30 mg chloramines-T in DI water, the second reagent vial 102 was filled with a 50 ml solution containing 1 g Lym-1 antibody, and the third reagent vial 104 was filled with 10 ml of 13170 mCi I-131 in 0.1M PBS, pH 7.4. A 23 ml silicon reaction tube 118 was used for this radiolabeling batch. An ion exchange column 122 was used to purify the resulting radiolabeled product. The flow rate for this configuration was 2.3 ml/min, which gave a 10 minute reaction time using the 23 ml reaction tube. The labeling efficiency for this batch was determined to be 95.6%.

EXAMPLE 4

Continuous, In-Line Radiolabeling and Purification of Ch-TNT-1/b Antibodies

This example reports the use of an ion exchange column to purify a second type of radiolabeled antibody prepared by the methods of the invention.

In this study, the protein to be labeled is the Ch-TNT-1/b antibody. Further details regarding TNT antibodies are provided in U.S. Pat. No. 6,071,491, entitled "Detection of Necrotic Malignant Tissue and Associated Therapy", which is specifically incorporated herein by reference in its entirety.

Ch-TNT-1/b antibodies were labeled with I-131 (sodium salt) using a similar configuration as described above in Example 3, with a 17 ml silicone reaction tube and a 3 ml Dowex ion exchange column. The volumes used for each of the reagents were as follows: 4 ml I-131, 4 ml antibody, and 22 ml chloramine-T, and their respective concentration are shown below in Table 2. The collection vial was filled with radioprotectants, including 1.4 to 1.5 g sodium ascorbate and 37 to 39 ml of 25% serum albumin. The resulting purified radiolabeled products were then diluted into 0.9% saline to achieve the final concentration. The results shown in Table 2 indicate a yield or labeling efficiency of 88% or higher with a 10 minute elution or reaction time using a configuration as illustrated in FIG. 10.

studies. The method can also be readily automated, and the invention can be used at the hospital.

The present invention thus provides effective new methods for labeling, particularly of proteins and antibodies. In light of the present teaching, it is now possible for the tubings, flow rate, contents of the collecting vial and so on to be adapted, and nonetheless achieve large scale production of commercial and biomedical quality labeled products, particularly antibodies.

All patents, patent applications, provisional patent applications and other publications mentioned in this specification are specifically incorporated herein by reference in their entireties.

All of the methods, apparatus and compositions disclosed herein can be executed, made and used without undue experimentation in light of the present disclosure. While the methods, apparatus and compositions of this invention have been described in detail with reference to certain preferred embodiments, it will be apparent to those of ordinary skill in the art that the present invention is not limited to those precise embodiments. Rather, in view of the present disclosure, it will be understood that many modifications and variations may be applied to the apparatus and compositions, and to the steps or in the sequence of steps of the methods described herein, without departing from the concept, spirit and scope of the invention. It will also be apparent that certain agents that are both chemically and biologically related may be substituted for the agents described herein while the same or similar results would be achieved. Furthermore, those of ordinary

TABLE 2

| Batch | Activity mCi | Chloramine-T mg | Antibody mg | Total Vol. mL | Reaction Time min | Residual Activity mCi | Yield mCi | Yield % |
|---|---|---|---|---|---|---|---|---|
| A | 2960 | 9.6 | 216 | 30 | 10 | 54 | 2564 | 88 |
| B | 3216 | 9.6 | 233 | 30 | 10 | 62 | 2910 | 92 |
| C | 3120 | 9.2 | 233 | 30 | 10 | 54 | 2759 | 89 |
| D | 2820 | 10.1 | 231 | 30 | 10 | 154 | 2543 | 90 |

In summary, and as exemplified by the foregoing working examples, the new inline labeling method of the present invention thus allows the rapid large scale production of therapeutic proteins and antibody doses of high quality. These methods are flexible to use in a variety of embodiments. The system can be adapted, e.g., by selecting the appropriate tubing, from a very small reaction volume to a very large scale with practically no limits. The continuous flow allows principally unlimited production batch sizes. This is important in moving from pre-clinical studies to small scale clinical trials to large scale patient treatment, as the same process can be used to prepare labeled therapeutics for a single patient or hundreds or thousands of patients, which is important to FDA approval for therapeutic production techniques.

Further advantages of the invention are that all the components of the apparatus can be prepared sterile and are disposable; the tubes can be removed from the pump and discarded, so that no routine cleaning is required. After very extended use, radiolysis will indicate that the tubing and purification means should be discarded and replaced. Nonetheless, operation of the present invention in continuous mode can be carried out for extended times that are impossible to reach using the batch labeling of prior art and existing methods. The reduced cost of the invention is also a significant benefit, with a cost saving of 10 to 30-fold predicted based upon the present skill in the art will recognize, or be able to ascertain, using no more than routine experimentation, many equivalents to the specific embodiments of the invention described herein. All such changes, modifications, variations, similar substitutes and equivalents coming within the meaning and range of equivalency of the claims are to be considered as encompassed within the scope of the claims.

The invention claimed is:

1. A continuous mode apparatus for labeling a molecule with a radioactive label, said apparatus comprising:
    a reaction chamber or tube comprising a first end and a second end;
    a first reagent vessel fluidly connected to said first end of said reaction chamber or tube through a first reagent tubing, said first reagent tubing connected to at least a first pump that moves fluid through said apparatus to achieve substantially continuous flow of fluid through said apparatus;
    a second reagent vessel fluidly connected to said first end of said reaction chamber or tube through a second reagent tubing, said second reagent tubing connected to a pump;
    a third reagent vessel fluidly connected to said first end of said reaction chamber or tube through a third reagent tubing, said third reagent tubing connected to a pump; and at least a first purification unit comprising an inlet and an outlet, said inlet of said purification unit fluidly connected to said second end of said reaction chamber or tube;

wherein said purification unit comprises a capture agent that captures an unattached or free radioactive label and an unattached or free molecule on the basis of size, charge or affinity, but allows a radiolabeled molecule to pass through.

2. The apparatus of claim 1, wherein said apparatus comprises a reaction tube.

3. The apparatus of claim 1, wherein said first reagent tubing and said second reagent tubing are each connected to said first pump.

4. The apparatus of claim 3, wherein said first reagent tubing, said second reagent tubing and said third reagent tubing are each connected to said first pump.

5. The apparatus of claim 4, Wherein said first pump is a multi-channel peristaltic pump.

6. The apparatus of claim 5, wherein said multi-channel peristaltic pump is controllable by a computer.

7. The apparatus of claim 1, wherein said apparatus further comprises a radioshield; and wherein at least one of said reagent vessels is comprised within said radioshield.

8. the apparatus of claim 1, wherein said purification unit comprises at least a first substance that binds iodine, mixed halogen species, and oxidized iodide species.

9. The apparatus of claim 1, wherein said purification unit comprises at least a first ion exchange column or size exclusion column.

10. The apparatus of claim 9, wherein said ion exchange column is an anion exchange column.

11. The apparatus of claim 1, wherein said purification unit comprises at least a first dialysis unit.

12. The apparatus of claim 1, wherein said apparatus further comprises at least a first dispensing unit or collection vessel fluidly connected to said outlet of said purification unit.

13. The apparatus of claim 12, wherein said apparatus further comprises a filter comprising an input end and an output end, said input end of said filter fluidly connected to said outlet of said purification unit; and said output end of said filter connected to said collection vessel.

14. A continuous mode apparatus for radiolabeling a molecule, said apparatus comprising:
a reaction chamber or tube comprising a first end and a second end;
a first reagent vessel fluidly connected to said first end of said reaction chamber or tube through a first reagent tubing, said first reagent tubing connected to a pump that moves fluid through said apparatus to achieve substantially continuous flow of fluid through said apparatus;
a second reagent vessel fluidly connected to said first end of said reaction chamber or tube through a second reagent tubing, said second reagent tubing connected to said pump;
a third reagent vessel fluidly connected to said first end of said reaction chamber or tube through a third reagent tubing, said reagent tubing connected to said pump; and
at least a first purification unit comprising an inlet and an outlet, said inlet of said purification unit fluidly connected to said second end of said reaction chamber or tube;
wherein said purification unit comprises a capture agent that captures an unattached or free radioactive label and an unattached or free molecule on the basis of size, charge or affinity, but allows a radiolabeled molecule to pass through.

15. The apparatus of claim 14, wherein said apparatus further comprises a radioshield; and wherein at least one of said reagent vessels is comprised within said radioshield.

16. A continuous mode apparatus for radiolabeling a molecule, said apparatus comprising:
a reaction chamber or tube comprising a first end and a second end;
a first reagent vessel fluidly connected to said first end of said reaction chamber or tube through a first reagent tubing, said first reagent tubing connected to a first pump that moves fluid through said apparatus to achieve substantially continuous flow of fluid through said apparatus;
a second reagent vessel fluidly connected to said first end of said reaction chamber or tube through a second reagent tubing, said second reagent tubing connected to a second pump that moves fluid through said apparatus to achieve substantially continuous flow of fluid through said apparatus;
a third reagent vessel fluidly connected to said first end of said reaction chamber or tube through a third reagent tubing, said reagent tubing connected to a third pump that moves fluid through said apparatus to achieve substantially continuous flow of fluid through said apparatus;
at least a first purification unit comprising an inlet and an outlet, said inlet of said purification unit fluidly connected to said second end of said reaction chamber or tube;
wherein said purification unit comprises a capture agent that captures an unattached or free radioactive label and an unattached or free molecule on the basis of size, charge or affinity, but allows a radiolabeled molecule to pass through.

17. The apparatus of claim 16, wherein each of said first, second and third pump is a peristaltic pump.

18. The apparatus of claim 17, wherein each of said first, second and third pump is controllable by a computer.

19. The apparatus of claim 16, wherein said apparatus further comprises a radioshield; and wherein at least one of said reagent vessels is comprised within said radioshield.

20. A continuous mode apparatus for radiolabeling a molecule with an oxidizable radioactive label, comprising:
a reaction chamber or tube comprising a first end and a second end;
a first reagent vessel containing an oxidizing agent; wherein said first reagent vessel is fluidly connected to said first end of said reaction chamber or tube through a first reagent tubing, said first reagent tubing passing through at least a first pump;
a second reagent vessel containing said molecule; wherein said second reagent vessel is fluidly connected to said first end of said reaction chamber or tube through a second reagent tubing, said second reagent tubing passing through a pump;
a third reagent vessel containing said oxidizable radioactive label; wherein said third reagent vessel is fluidly connected to said first end of said reaction chamber or tube through a third reagent tubing, said third reagent tubing passing through a pump; and
at least a first purification unit comprising an inlet and an outlet, said inlet of said purification unit fluidly connected to said second end of said reaction chamber or tube;

wherein said purification unit comprises a capture agent that captures an unattached or free oxidizable radioactive label and an unattached or free molecule on the basis of size, charge or affinity, but allows a radiolabeled molecule to pass through;

wherein said molecule, said oxidizable radioactive label and said oxidizing agent substantially continuously flow through said reaction chamber or tube.

21. The apparatus of claim 20, wherein said apparatus further comprises a radioshield; and wherein said third reagent vessel containing said oxidizable radioactive label is comprised within said radioshield.

22. A method of making a continuous mode apparatus for radiolabeling a molecule, said method comprising:

providing at least a first reagent vessel, a second reagent vessel and a third reagent vessel;

providing a reaction chamber or tube comprising a first end and a second end;

providing at least a first pump that moves fluid through said apparatus to achieve substantially continuous flow of fluid through said apparatus;

providing at least a first purification unit comprising an inlet, an outlet and a capture agent; wherein said capture agent is capable of capturing an unattached or free radioactive label and an unattached or free molecule on the basis of size, charge or affinity, but allows a radiolabeled molecule to pass through;

fluidly connecting said first reagent vessel to said first end of said reaction chamber or tube using a first reagent tubing, said first reagent tubing connected to said at least a first pump;

fluidly connecting said second reagent vessel to said first end of said reaction chamber or tube using a second reagent tubing, said second reagent tubing connected to a pump;

fluidly connecting said third reagent vessel to said first end of said reaction chamber or tube using a third reagent tubing, said third reagent tubing connected to a pump; and fluidly connecting said second end of said reaction tube to said inlet of said purification unit.

23. The method of claim 22, further comprising providing at least a first dispensing unit or collection vessel; and fluidly connecting said outlet of said purification unit to said at least a first dispensing unit or collection vessel.

24. The method of claim 22, wherein said at least a first pump is a peristaltic pump having at least a first and second channel.

25. The method of claim 24, wherein said first reagent tubing and said second reagent tubing are connected to said first and second channel of said peristaltic pump.

26. The method of claim 24, wherein said peristaltic pump further includes a third channel.

27. The method of claim 26, wherein said third reagent tubing is connected to said third channel of said peristaltic pump.

* * * * *